US008226602B2

(12) United States Patent
Quijana et al.

(10) Patent No.: US 8,226,602 B2
(45) Date of Patent: Jul. 24, 2012

(54) INTRAGASTRIC BALLOON SYSTEM AND THERAPEUTIC PROCESSES AND PRODUCTS

(75) Inventors: Rodolfo C. Quijana, Laguna Hills, CA (US); Andrew H. Cragg, Edina, MN (US); Hosheng Tu, Newport Beach, CA (US); Stephen A. Sosnowski, Vista, CA (US); George Wallace, Coto de Caza, CA (US)

(73) Assignee: ReShape Medical, Inc., San Clemente, CA (US)

( * ) Notice: Subject to any disclaimer, the term of this patent is extended or adjusted under 35 U.S.C. 154(b) by 931 days.

(21) Appl. No.: 11/694,536

(22) Filed: Mar. 30, 2007

(65) Prior Publication Data

US 2008/0243071 A1    Oct. 2, 2008

(51) Int. Cl.
*A61M 31/00* (2006.01)
*A61M 37/00* (2006.01)

(52) U.S. Cl. .................................................. 604/103.02
(58) Field of Classification Search .............. 604/65–68, 604/890.1, 96.01, 101.03, 101.04, 101.05, 604/102.01, 103.01, 103.02, 101.01; 606/192
See application file for complete search history.

(56) References Cited

U.S. PATENT DOCUMENTS

| | | | |
|---|---|---|---|
| 2,493,326 A | 1/1950 | Trinder | |
| 4,133,315 A | 1/1979 | Berman et al. | |
| 4,246,893 A | 1/1981 | Berson | |
| 4,356,824 A | 11/1982 | Vazquez | |
| 4,368,739 A * | 1/1983 | Nelson, Jr. | 604/516 |
| 4,416,267 A | 11/1983 | Garren et al. | |
| 4,485,805 A | 12/1984 | Foster, Jr. | |
| 4,598,699 A | 7/1986 | Garren et al. | |
| 4,694,827 A | 9/1987 | Weiner et al. | |
| 4,723,547 A | 2/1988 | Kullas et al. | |
| 4,899,747 A | 2/1990 | Garren et al. | |
| 5,084,061 A | 1/1992 | Gau et al. | |
| 5,123,840 A | 6/1992 | Nates | |
| 5,259,399 A | 11/1993 | Brown | |
| 5,263,934 A | 11/1993 | Haak | |
| 5,318,530 A * | 6/1994 | Nelson, Jr. | 604/103.1 |
| 5,334,187 A | 8/1994 | Fischell et al. | |
| 5,431,173 A | 7/1995 | Chin et al. | |
| 5,496,271 A | 3/1996 | Burton et al. | |
| 5,575,772 A | 11/1996 | Lennox | |
| 5,730,722 A * | 3/1998 | Wilk | 604/507 |
| 5,779,728 A | 7/1998 | Lunsford et al. | |
| 5,857,991 A | 1/1999 | Grothoff et al. | |

(Continued)

FOREIGN PATENT DOCUMENTS

EP    0 457 456    5/1990

(Continued)

OTHER PUBLICATIONS

Wahlen CH et al. "The BioEnterics Intragastric Balloon: How to use it" Obesity Surgery 2001;11:524-527.

(Continued)

*Primary Examiner* — Christopher D Koharski
(74) *Attorney, Agent, or Firm* — Perkins Coie LLP

(57) ABSTRACT

A gastric space filler device for treating obesity in a patient by reducing the stomach volume features at least one inflatable space filler with drag delivery and stimulation features and includes therapeutic devices and anchoring apparatus enabling tracking, visualization and optimized management of inter-balloon connecting sections, drug reservoirs and pumping systems along with related improvements.

29 Claims, 14 Drawing Sheets

U.S. PATENT DOCUMENTS

| | | | |
|---|---|---|---|
| 5,938,669 | A | 8/1999 | Klaiber et al. |
| 5,993,473 | A | 11/1999 | Chan |
| 6,149,621 | A | 11/2000 | Makihara |
| 6,254,355 | B1 | 7/2001 | Gharib |
| 6,276,567 | B1 | 8/2001 | Diaz et al. |
| 6,280,411 | B1 * | 8/2001 | Lennox ............. 604/103.05 |
| 6,423,058 | B1 | 7/2002 | Edwards et al. |
| 6,454,785 | B2 | 9/2002 | De Hoyos Garza |
| 6,535,764 | B2 | 3/2003 | Imran et al. |
| 6,547,788 | B1 | 4/2003 | Maguire et al. |
| 6,579,301 | B1 | 6/2003 | Bales et al. |
| 6,613,018 | B2 | 9/2003 | Bagga et al. |
| 6,613,037 | B2 | 9/2003 | Khosravi et al. |
| 6,746,460 | B2 | 6/2004 | Gannoe et al. |
| 6,826,428 | B1 | 11/2004 | Chen et al. |
| 6,850,128 | B2 | 2/2005 | Park |
| 6,866,657 | B2 | 3/2005 | Shchervinsky et al. |
| 6,890,300 | B2 | 5/2005 | Lloyd et al. |
| 6,923,754 | B2 | 8/2005 | Lubock |
| 6,939,299 | B1 | 9/2005 | Petersen et al. |
| 7,001,419 | B2 | 2/2006 | DiCaprio et al. |
| 7,016,735 | B2 | 3/2006 | Imran et al. |
| 7,020,531 | B1 | 3/2006 | Colliou et al. |
| 7,033,373 | B2 | 4/2006 | de la Torre et al. |
| 7,056,305 | B2 | 6/2006 | Garza Alvarez |
| 7,076,305 | B2 | 7/2006 | Imran et al. |
| 7,131,945 | B2 | 11/2006 | Fink et al. |
| 7,483,746 | B2 * | 1/2009 | Lee et al. ............. 607/40 |
| 2001/0037127 | A1 | 11/2001 | De Hoyos Garza |
| 2002/0055757 | A1 | 5/2002 | Torre |
| 2002/0161388 | A1 | 10/2002 | Samuels et al. |
| 2002/0173804 | A1 | 11/2002 | Rousseau |
| 2003/0114878 | A1 | 6/2003 | Diederich et al. |
| 2003/0171768 | A1 | 9/2003 | McGhan |
| 2003/0187390 | A1 | 10/2003 | Bates et al. |
| 2004/0044354 | A1 | 3/2004 | Gannoe et al. |
| 2004/0059289 | A1 | 3/2004 | Garza Alvarez |
| 2004/0059290 | A1 * | 3/2004 | Palasis ............. 604/101.01 |
| 2004/0087902 | A1 * | 5/2004 | Richter ............. 604/103.02 |
| 2004/0116897 | A1 | 6/2004 | Aboul-Hosn |
| 2004/0127915 | A1 | 7/2004 | Fleenor et al. |
| 2004/0186502 | A1 | 9/2004 | Sampson |
| 2004/0236280 | A1 | 11/2004 | Rice et al. |
| 2004/0254600 | A1 | 12/2004 | Zarbatany et al. |
| 2005/0027283 | A1 | 2/2005 | Richard et al. |
| 2005/0038415 | A1 * | 2/2005 | Rohr et al. ............. 604/891.1 |
| 2005/0059990 | A1 | 3/2005 | Ayala et al. |
| 2005/0075624 | A1 * | 4/2005 | Miesel ............. 604/505 |
| 2005/0085792 | A1 | 4/2005 | Gershowitz |
| 2005/0119674 | A1 | 6/2005 | Gingras |
| 2005/0143784 | A1 | 6/2005 | Imran |
| 2005/0159769 | A1 | 7/2005 | Alverdy |
| 2005/0177103 | A1 * | 8/2005 | Hunter et al. ............. 604/96.01 |
| 2005/0192615 | A1 | 9/2005 | Torre et al. |
| 2005/0267595 | A1 | 12/2005 | Chen et al. |
| 2005/0267596 | A1 | 12/2005 | Chen et al. |
| 2006/0058829 | A1 | 3/2006 | Sampson et al. |
| 2006/0184112 | A1 * | 8/2006 | Horn et al. ............. 604/103.08 |
| 2006/0259020 | A1 | 11/2006 | Sharratt |
| 2007/0016262 | A1 | 1/2007 | Gross et al. |
| 2007/0100367 | A1 | 5/2007 | Quijano |
| 2007/0100368 | A1 | 5/2007 | Quijano |
| 2007/0100369 | A1 | 5/2007 | Cragg |
| 2007/0142770 | A1 | 6/2007 | Rioux et al. |
| 2007/0149994 | A1 | 6/2007 | Sosnowski |
| 2007/0173881 | A1 | 7/2007 | Birk et al. |
| 2007/0250020 | A1 | 10/2007 | Kim et al. |
| 2007/0288033 | A1 | 12/2007 | Murature et al. |
| 2008/0058887 | A1 | 3/2008 | Griffin et al. |
| 2008/0082056 | A1 | 4/2008 | Mauch et al. |
| 2008/0097513 | A1 | 4/2008 | Kaji et al. |
| 2008/0119729 | A1 | 5/2008 | Copa et al. |
| 2008/0172079 | A1 | 7/2008 | Birk |
| 2008/0190363 | A1 | 8/2008 | Chen et al. |
| 2008/0208241 | A1 | 8/2008 | Weiner et al. |
| 2008/0233167 | A1 | 9/2008 | Li et al. |
| 2008/0243071 | A1 | 10/2008 | Quijano et al. |
| 2008/0243166 | A1 | 10/2008 | Paganon et al. |
| 2008/0255601 | A1 | 10/2008 | Birk |
| 2008/0319471 | A1 | 12/2008 | Sosnowski |
| 2009/0048624 | A1 | 2/2009 | Alverdy |
| 2009/0275973 | A1 | 11/2009 | Chen et al. |
| 2010/0023047 | A1 | 1/2010 | Simpson |
| 2010/0130998 | A1 | 5/2010 | Alverdy |
| 2010/0243135 | A1 | 9/2010 | Pepper et al. |
| 2011/0178544 | A1 | 7/2011 | Sosnowski et al. |

FOREIGN PATENT DOCUMENTS

| | | |
|---|---|---|
| EP | 0 485 903 | 8/1991 |
| FR | 2862525 A1 | 5/2005 |
| GB | 2 139 902 A | 11/1984 |
| WO | WO 2006035446 | 4/2006 |
| WO | WO 2006/128978 | 12/2006 |
| WO | WO-2009112786 A2 | 9/2009 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011038270 A2 | 3/2011 |
| WO | WO2011024077 | 8/2011 |
| WO | WO2011097637 | 8/2011 |
| WO | WO2011127205 | 10/2011 |

OTHER PUBLICATIONS

Patient information "Living with the BIB" by INAMED Health (2004).

International Search Report; International Application No. PCT/US2008/058677, Applicant: ReShape Medical et al., Mailing Date Aug. 21, 2008, 12 pages.

International Search Report; International Application No. PCT/US2006/042710, Applicant: Abdominus, Inc. et al., Mailing Date Mar. 15, 2007, 9 pages.

International Search Report; International Application No. PCT/US2006/048647, Applicant: Abdominus, Inc. et al., Mailing Date May 22, 2007, 12 pages.

International Search Report; International Application No. PCT/US2008/068058, Applicant: ReShape Medical, Inc. et al, Mailing Date Nov. 19, 2008, 11 pages.

International Search Report; International Application No. PCT/US2006/042711, Applicant: Abdominus, Inc. et al, Mailing Date Mar. 16, 2007, 9 pages.

Supplementary European Search Report for EP 03726447.0, mailed Mar. 1, 2006.

International Search Report; International Application No. PCT/US2003/012782, Applicant: Applied Medical Resources Corporation, Mailing Date Oct. 28, 2003, 7 pages.

International Search Report; International Application No. PCT/US2006/042336, Applicant: Abdominus, Inc., Mailing Date Mar. 14, 2007, 9 pages.

International Search Report; International Application No. PCT/US2010/029865, Applicant: ReShape Medical, Inc., Mailing Date Jan. 5, 2011, 9 pages.

Final Office Action; U.S. Appl. No. 11/768,152, Mailing Date Jan. 19, 2011, 13 pages.

International Search Report; International Application No. PCT/US2011/024082, Applicant: ReShape Medical, Inc., Mailing Date Apr. 6, 2011, 10 pages.

International Search Report; International Application No. PCT/US2011/024077; Applicant: ReShape Medical, Inc., Mailing Date Apr. 6, 2011, 12 pages.

International Search Report; International Application No. PCT/US2010/042948; Applicant: ReShape Medical, Inc., Mailing Date Apr. 1, 2011, 11 pages.

International Search Report; International Application No. PCT/US2010/043136; Applicant: ReShape Medical, Inc., Mailing Date Apr. 12, 2011, 9 pages.

International Search Report; International Application No. PCT/US2010/043134; Applicant: ReShape Medical, Inc., Mailing Date Apr. 27, 2011, 12 pages.

International Search Report; International Application No. PCT/US2011/0426233; Applicant: ReShape Medical, Inc., Mailing Date Apr. 26, 2011, 9 pages.

"ReShape Inflatable Gastric Ballon Going on Trial as Weight Loss Option," MedGadget: Internet Journal of Emerging Medical Technologies. Feb. 4, 2010. (5 pages).

International Search Report; International Application No. PCT/US2010/050260; Applicant: ReShape Medical, Inc., Mailing Date: Jun. 17, 2011, 9 pages.

International Search Report; International Application No. PCT/US2011/031463; Applicant: ReShape Medical, Inc., Mailing Date: Jun. 27, 2011, 10 pages.

International Search Report and Written Opinion; International Application No. PCT/US1155373, Applicant: Reshape Medical, Inc., Mailing Date Jan. 20, 2012, 7 pages.

Non-Final Office Action; U.S. Appl. No. 12/625,473; Mailing Date Oct. 24, 2011, 18 pages.

* cited by examiner

INTRAGASTRIC BALLOON SYSTEM AND THERAPEUTIC PROCESSES AND PRODUCTS

CROSS-REFERENCE TO RELATED APPLICATIONS

This application is related to U.S. patent application (a) Ser. No. 11/263,302, filed Oct. 21, 2005, (b) Ser. No. 11/262,614, filed Oct. 31, 2005, (c) Ser. No. 11/315,925, filed Dec. 22, 2005, and (d) Ser. No. 11/452,670, filed Jun. 14, 2006, the entire contents EACH of which ate incorporated herein by reference, expressly as if fully set forth herein.

FIELD OF THE INVENTION

The present invention is generally related to implantable weight control devices. More particularly, the present invention is related to devices and methods for reducing nausea caused by intragastric balloons for treatment of morbid obesity.

BACKGROUND

Gastric space fillers used for achieving loss of weight in extremely obese persons have been known in the prior art. All gastric space fillers utilized for this purpose function on the principles that an empty bag or space filler is placed into the stomach through the esophagus. Thereafter, the bag or space filler is filled (fully or partially) with a suitable insufflation fluid, such as saline solution, through a filler tube or catheter, which is inserted into the stomach through the mouth or the nose. The space filler occupies space in the stomach thereby leaving less room available for food and creating a feeling of satiety for the obese person. Clinical experience of the prior art has shown that for many obese patients the intragastric space fillers significantly help to control appetite and accomplish weight loss.

Garten et al in U.S. Pat. Nos. 4,416,267 and 4,899,747, entire contents of which are incorporated herein by reference, discloses a stomach insert for treating obesity in humans by reducing the stomach volume comprising a flexible, torus-shaped inflatable space filler having a central opening extending therethrough. At least a portion of the space filler has a self-sealing substance to facilitate puncture thereof with a needle for inflating the space filler and sealing off the puncture upon removal of the needle. The method herein comprises positioning the space filler inside the stomach of the person being treated for obesity so as to reduce the stomach volume. The Garten et al. stomach insert works satisfactorily to control the appetite. However, the insert may cause nausea and uncomfortable side effects. It appears desirable to have a space filler system that could reduce nausea caused by intragastric balloons for treatment of morbid obesity of a patient.

Several surgical techniques have been tried which bypass the absorptive surface of the small intestine or aim at reducing the stomach size by either partition or bypass. These procedures have been proven both hazardous to perform in morbidly obese patients and have been fraught with numerous life-threatening postoperative complications. Moreover, such operative procedures are often difficult to reverse.

Non-surgical approaches for the treatment of obesity include voluntary dieting which is often unsuccessful since most persons do not possess sufficient willpower to limit the intake of food. Other approaches include the use of stomach fillers such as methylcellulose (MC), often taken in the form of tablets. The methylcellulose expands in the stomach leaving the person with a filled-up feeling. Also, inflatable bag and tube combinations have been proposed wherein the bag is swallowed into the stomach and the tube attached thereto is used to periodically inflate the bag, particularly just prior to mealtime or during the meal. Once the person has eaten, the bag can be deflated all at once, or it can be deflated gradually over a period of a few hours so as to simulate the condition of digestion occurring and the gradual reduction of stomach contents.

Methylcellulose (MC) is a water-soluble polymer derived from cellulose, the most abundant polymer in nature. As a viscosity-enhancing polymer, it thickens a solution without precipitation over a wide pH range. These functional hydrogels may change their structures as they expose to varying environment, such as temperature, pH, or pressure. MC gels from aqueous solutions upon heating or salt addition (*Langmuir* 2002; 18:7291, *Langmuir* 2004; 20:6134). This unique phase-transition behavior of MC enables it a promising functional hydrogel for various biomedical applications (*Biomaterials* 2001; 22:1113, *Biomacromolecules* 2004; 5:1917. Tate et al studied the use of MC as a thermoresponsive scaffolding material (*Biomaterials* 2001; 22:1113. In their study, MC solutions were produced to reveal a low viscosity at room temperature and formed a soft gel at 37° C.; thus making MC well suited as an injectable swellable material. Additionally, using its thermoresponsive feature, MC was reported to harden aqueous alginate as a pH-sensitive based system for the delivery of protein drugs (*Biomacromolecules* 2004; 5:1917. Some aspects of the invention provide a method and material to fill an internal space of the filler with swellable hydrogel (such as methylcellulose), wherein the hydrogel is a temperature sensitive or pH sensitive hydrogel.

U.S. Pat. No. 4,133,315 issued on Jan. 9, 1979, entire contents of which are incorporated herein by reference, discloses an inflatable bag and tube combination. The tubing remains attached to the bag and inside the esophagus of the person being treated. These tubes are often the cause of erosions and ulcerations of the esophagus. This patent also discloses a gastronomy method, wherein the permanently attached tube used to distend the stomach bag extends through an opening in the stomach wall as well as an opening in the abdomen.

U.S. Pat. No. 4,246,893 issued on Jan. 27, 1981, entire contents of which are incorporated herein by reference, discloses an inflatable bag and tube combination, which is surgically positioned outside and adjacent to the stomach. Upon inflation of the bag, the upper abdomen is distended and the stomach compressed to produce a sense of satiety, which reduces the person's desire to ingest food.

U.S. Pat. No. 4,598,699 issued on Jul. 8, 1996, entire contents of which are incorporated herein by reference, discloses an endoscopic instrument for removing an inflated insert from the stomach cavity of a person being treated for obesity comprising an elongated flexible tube having passageways therein and a holding device at the distal end of the flexible tube that is constructed and arranged to grasp and stabilize the inflated stomach insert.

Certain prior art discloses a gastric stimulator apparatus for stimulating neuromuscular tissue in the stomach, for example, U.S. Pat. No. 6,826,428 issued on Nov. 30, 2004. In one disclosure, it provides a method of regulating gastrointestinal action using a stimulatory electrode and a sensor to provide retrograde feedback control of electrical stimulation to the GI tract or to the stomach.

U.S. Pat. No. 7,020,531 issued on Mar. 28, 2006, entire contents of which are incorporated herein by reference, discloses a device for electrical stimulation of the stomach wall.

The device may also have other functional aspects such as a sensor for sensing various parameters of the stomach or stomach environment, or a substance delivery device. In one embodiment, an endoscopic delivery system delivers the functional device thorough the esophagus and into the stomach where it is attached to the stomach wall with the assistance of a suction used to stabilize the tissue of the stomach wall.

U.S. Pat. No. 6,535,764 issued on Mar. 18, 2003, U.S. Pat. No. 7,016,735 issued on Mar. 21, 2006, and U.S. Pat. No. 7,076,305 issued on Jul. 11, 2006, entire contents of which are incorporated herein by reference, disclose a gastric stimulation device comprising: a housing; electronic circuitry contained within the housing; at least one stimulating electrode coupled to the housing and electrically coupled to the electronic circuitry; and an attachment device coupled to the housing and operative to attach the housing within a stomach cavity to a stomach wall so that the at least one stimulating electrode is in electrical contact with the stomach wall; wherein the electronic circuitry is configured to deliver electrically stimulating signals to the stomach through the at least one stimulating electrode.

U.S. Pat. No. 4,694,827 issued on Sep. 22, 1987, entire contents of which are incorporated herein by reference, discloses a balloon insertable and inflatable in the stomach to deter ingestion of food and having, when inflated, a plurality of smooth-surfaced convex protrusions disposed to permit engagement of the stomach wall by the balloon only at spaced localities, for minimizing mechanical trauma of the stomach wall by the balloon.

U.S. Pat. No. 6,746,460 issued on Jun. 8, 2004, entire contents of which are incorporated herein by reference, discloses an expandable device that is inserted into the stomach of the patient that is maintained within by anchoring or otherwise fixing the expandable device to the stomach walls. Such expandable devices have tethering regions for attachment to the one or more fasteners, which can be configured to extend at least partially through one or several folds of the patient's stomach wall. Such fasteners can be formed in a variety of configurations (e.g., helical, elongate, ring, clamp) and they, can be configured to be non-piercing.

Hence, reducing the size of the gastric compartment has been shown to induce weight loss in a significant percentage of people, and the present invention is aimed at a device which non-operatively reduces the size of the gastric compartment and which is easily removed. Further, the invention discloses a gastric space filler device with drug release capability and/or stimulation capability. One aspect of the invention relates to an intragastric balloon system with means for reducing nausea caused by the implant.

SUMMARY

In accordance with preferred embodiments of the present invention, some aspects of the invention relate to a gastric space filler system for treating obesity in a patient by reducing the stomach volume comprising at least two flexible inflatable space fillers secured to each other, a first space filler being inflatable to a volume inside the stomach and not in fluid communication with the other remaining space fillers, and a drug delivery mechanism. In one embodiment, the drug delivery mechanism comprises a drug reservoir, a drug-releasing pump attached to the drug reservoir, and a marker sensor for triggering the drag-releasing pump for drug dispensing.

In one embodiment, the space filler system comprises a pressure reading device for transmitting internal pressure readings of the stomach to a receiver or controller. In a further embodiment, a pressure sensor element is mounted on the gastric space filler system for sensing an internal pressure of the stomach. In a further embodiment, the pressure sensor element further comprises a transmitter for wirelessly transmitting the measured internal pressure signal to a receiver outside a body of the patient. The measured internal pressure is compared to a pre-determined threshold pressure for signaling release of the drug from the drug reservoir. In some embodiment, a pH sensor, a flow-rate sensor, a temperature sensor, an electrolyte sensor, or the like may substitute for the pressure sensor element.

In one embodiment, at least one of the two space fillers of the gastric space filler system is anchored to an inner wall of the stomach. In a further embodiment, the anchoring action is arranged and configured to activate the anchoring mechanism when the space filler is inflated while contacting the inner wall of the stomach, and to reverse the anchoring mechanism when the filler is deflated. There is likewise provided an electric stimulator (electrode) located on the filler system, wherein the electrode is configured at the contacting point or site of the stomach wall.

In a further embodiment, at least a portion of the at least two-balloon filler system is ultrasonically visible. One method of visualization is to have ultrasonically visible air bubble at or on part of the space filler. Another method is to incorporate ultrasonically visible contrast agent at or on part of the space filler.

In one embodiment, the biodegradable material for the drug-containing coating on the gastric space filler system is selected from a group consisting of polymers or copolymers of lactide, glycolide, caprolactone, polydioxanone, trimethylene carbonate, polyorthoesters and polyethylene oxide.

Some aspects of the invention provide a method of treating obesity in a patient with minimal nausea effects comprising implanting a stomach space filler device coated with an anti-nausea agent or loaded with anti-nausea drug.

Some aspects of the invention provide a system for providing therapy to a gastrointestinal system of a patient, comprising: a gastric space filler, at least one therapeutic means, and an anchoring means for anchoring the at least one therapeutic means to the space filler. In one embodiment, the therapeutic means is selected from the group consisting of (a) a drug reservoir loaded with a drug for drug release to the stomach or the intestine of the gastrointestinal system, (b) an electric stimulation assembly for providing electric stimulation to the stomach or the intestine of the gastrointestinal system, (c) a mechanical motion assembly for providing mechanical massage to the stomach or the intestine of the gastrointestinal system, (d) an absorption inhibition means for inhibiting food absorption to the stomach or the intestine of the gastrointestinal system, (e) a sensor or diagnostic instrument for sensing a signal or diagnosing a symptom in the stomach or the intestine of the gastrointestinal system, (f) a nutrition delivery setup loaded with a nutrition for nutrition release to the stomach or the intestine of the gastrointestinal system, and (g) a small bowel therapy.

DRAWINGS

Additional objects and features of the present invention will become more apparent and the invention itself will be best understood from the following Detailed Description of Exemplary Embodiments, when read with reference to the accompanying drawings.

DETAILED DESCRIPTION

Figure 1:
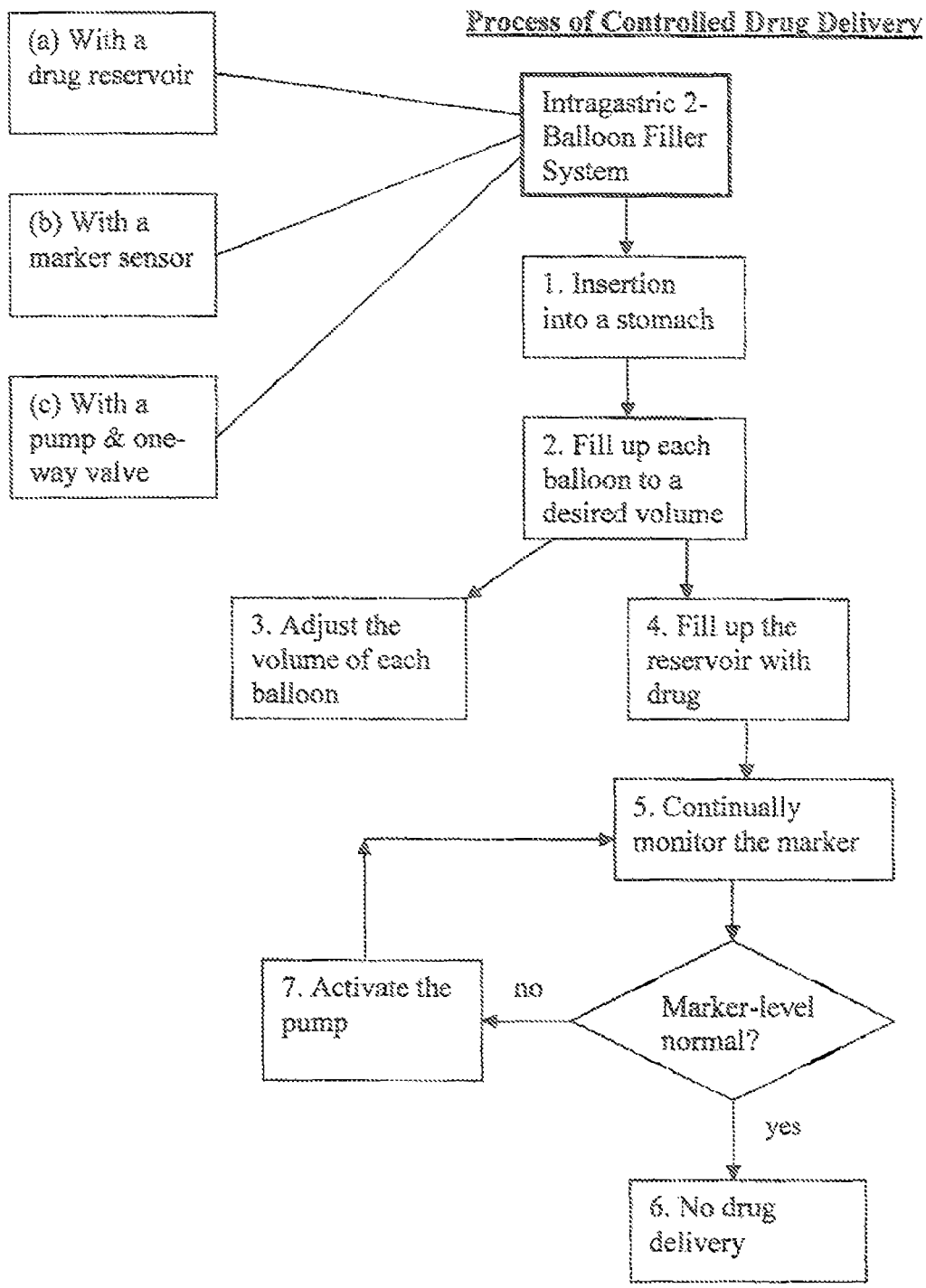
FIG. 1 shows a schematic flow-chart for controlled, drug delivery on-demand from a 2-balloon gastric space filler system.

Exemplary, but not limiting, embodiments of the present invention described below relate particularly to an intragastric space filler system comprising a drug delivery mechanism and/or electrical stimulation mechanism for treating obesity. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Medical complications of obesity may relate to one or more of the following indications; pulmonary disease (abnormal function, obstructive sleep apnea, hypoventilation syndrome), idiopathic intracranial hypertension, stroke, cataracts, nonalcoholic fatty liver disease (steatosis, steatohepatitis, cirrhosis), coronary heart disease, diabetes, dyslipidemia, hypertension, severe pancreatitis, gall bladder disease, cancer (breast, uterus, cervix, colon, esophagus, pancreas, kidney, prostate), gynecologic abnormalities (abnormal menses, infertility, polycystic ovarian syndrome), osteoarthritis, phlebitis (venous stasis), skin and gout. An intragastric balloon system of the present invention is to provide therapeutic means for managing or treating the above-cited indications.

The stomach has many functions and one of these is to expand and contract. This J-shaped organ has extremely active muscles. These muscles expand and contract depending on how much food is in the stomach. This contraction is a form of mechanical breakdown of the food. The purpose of this breakdown is to increase the available surface area for the chemicals to act on it. The gastric glands of the stomach secrete enzymes that perform chemical breakdown, partly digesting the proteins. Pepsin is the enzyme that breakdowns protein. The gastric gland also secretes hydrochloric acid that kills almost all the bacteria in the food, and helps digestion by breakdown of acid-labile proteins. It also secretes mucus that protects the stomach wall from the hydrochloric acid. By the time all the food is mechanically and chemically broken down, the food becomes a semi-fluid substance that leaves the stomach by peristalsis entering the small intestine.

The structure of the stomach is quite unique. It can be divided into four subdivisions: the cardia, the fundus, the body, and the pylorus. The cardia is the region that is closest to the heart and is where the esophagus is connected to the stomach. The fundus is the region that curves above the rest of the stomach (with respects to a person who is standing upward). The body of the stomach is the largest region located in the center. The pylorus is the region that is connected to the small intestine. The cardia and the pylorus have sphincter muscles that regulate the movement of food and fluids. The hydrochloric acid normally does not go back up the esophagus. When one vomits and has a burning sensation in the esophagus, it is the hydrochloric acid from the stomach.

The volume of the human stomach varies depending on the person. Generally, human stomachs have a volume about one liter. Since the stomach has the ability to expand, it can hold much more food. The human stomach can be distended up to four liters, which is more than one gallon. Imagine your stomach to be an empty one-gallon milk carton. There is plenty room for food.

2-Balloon Space Filler System

FIGS. 1-14 show one or an alternate embodiment of a gastric space filler device, methods of manufacture, and mechanisms for drug delivery, electrical stimulation, and other therapies. The intragastric balloon system of the present invention may serve as a therapeutic means or serve as an anchoring means for anchoring other therapeutic means on the system. The therapeutic means may be for, but not limited to, drug release, electric stimulation, mechanical motion, absorption inhibition, sensors or diagnostic instruments, nutrition delivery, and small bowel therapy. One embodiment is to employ the balloon system as a reservoir for drug or nutrition release via surface coating, enclosed pouches or a pumping mechanism.

FIG. 1 shows a schematic flow-chart for controlled drug delivery on-demand from a 2-balloon gastric space filler system. The gastric filler system of the present invention may contain one or more balloons, or balloon-type fillers. In one embodiment, the system comprises a drug reservoir, a pump for dispensing the drug from the drug reservoir, and a sensor for sensing the surrounding parameter and triggering delivery of the drug as desired. In use, an intragastric 2-balloon filler system is inserted via a delivery catheter through esophagus and cardiac notch into the stomach of a patient. Both balloons of the gastric space filler system are deflated, collapsed and retracted within a catheter sheath during the delivery phase or the retrieval phase of the device. Each balloon is filled up with saline or other fluid to a desired volume whereas the volume is adjustable. Through, a separate lumen in the same delivery catheter or through a filling tube, the reservoir is loaded with liquid drug. The sensor continuously monitors the marker or parameter to check if the marker-level is normal compared to a pre-determined value. The pump attached to the drug reservoir is triggered for drug release.

The pumping mode may be intermittent, continuous, or one-shoot only. The marker or parameters for triggering drug delivery may include pH, temperature, pressure, electrolyte concentration, electrolyte type, peptide or other biochemical signals. The pump may include centrifugal axial, pulsatile, rotary, combination of centrifugal and axial, and others. For example, Mortezs Gharib disclosed a hydro elastic pump that pumps using non-rotary bladeless and valveless operations (U.S. Pat. No. 6,254,355). For example, Diaz et al. disclosed a fluid delivery apparatus including a pressure tube and a first cap assembly coupled to a first end of the pressure tube and a second cap assembly coupled to a second end of the pressure tube, with the second cap assembly supporting a fluid container that is housed in the interior space of the pressure tube (U.S. Pat. No. 6,276,567).

In general, activation of the pumping mechanism may also be initiated by the patient in the absence of any signals from the interior of the stomach. At the onset of nausea, the patient can turn on a hand-held radiofrequency emitter that would be tuned to deliver the required amount of drug (for example, anti-emetic drug solution, anti-nausea agent, hormones known to produce feeling of satiety, and the like) as patient experiences the feeling of wanting to vomit or associated automatic effects of symptoms, such as hypersalivation, pallor, sweating, retching. Likewise, the matter (parameter) for triggering drug delivery may be at least one of plt, p, t, electrolyte, peptide or biochemicals. Artisans understand how each of these work.

Figure 2:
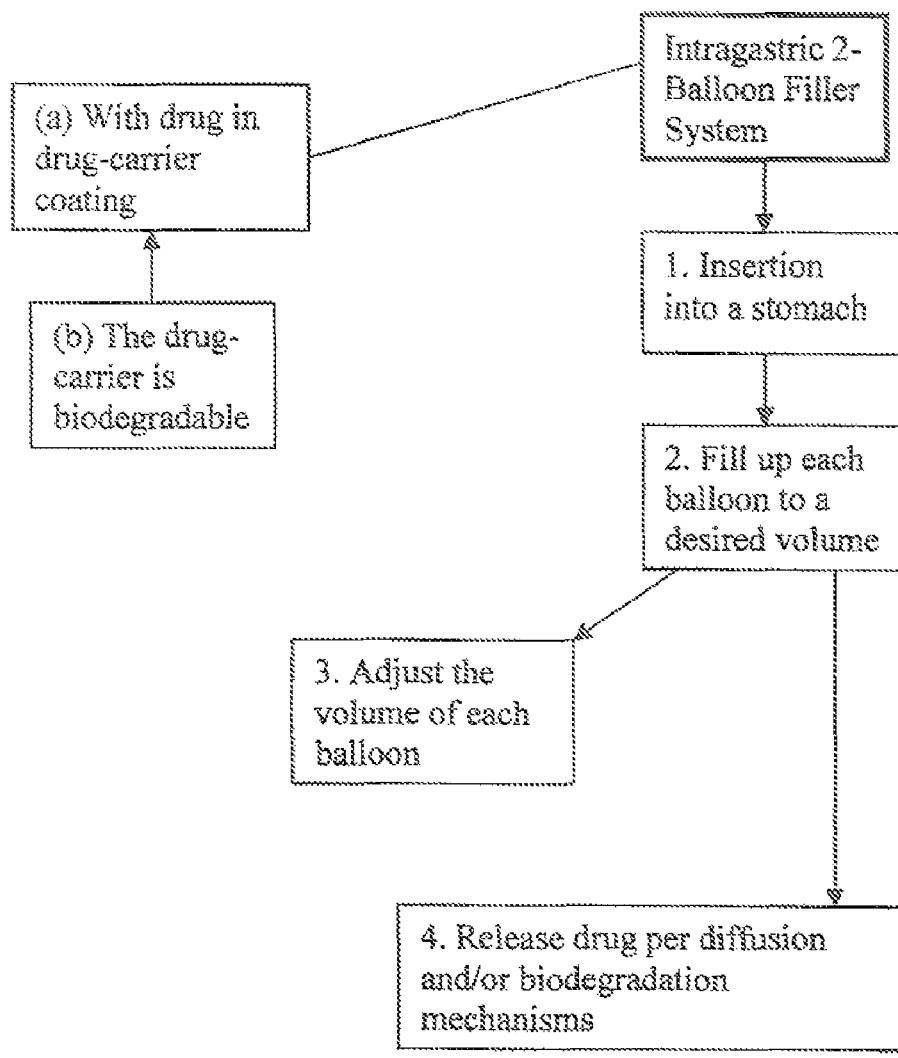
FIG. 2 shows a schematic flow-chart for sustained drag delivery from a 2-balloon gastric space filler system.

FIG. 2 shows a schematic flow-chart for sustained drug delivery from a 2-balloon gastric space filler system. In one embodiment, the intragastric 2-balloon filler system comprises drug coating (a layer, a line or a cluster) onto at least a portion of the exterior surface of the balloon, wherein the drug coating includes a drug carrier with loaded drug. The drug carrier is generally biocompatible with similar elasticity of the balloon material. The drug carrier may be non-biodegradable (such as silicone, polyurethane) for drug to diffuse through the carrier. In an alternate embodiment, the drug carrier is biodegradable. The biodegradable material may be selected from a group consisting of polymers or copolymers of lactide, glycolide, caprolactone, polydioxanone, trimethylene carbonate, polyorthoesters, and polyethylene oxide. In another embodiment, the biodegradable material is selected from a group consisting of collagen, chitosan, elastin, gelatin, and combinations thereof. In use, the drug continues to release from the filler system for a pre-determined period after being inserted into the stomach.

Figure 3:
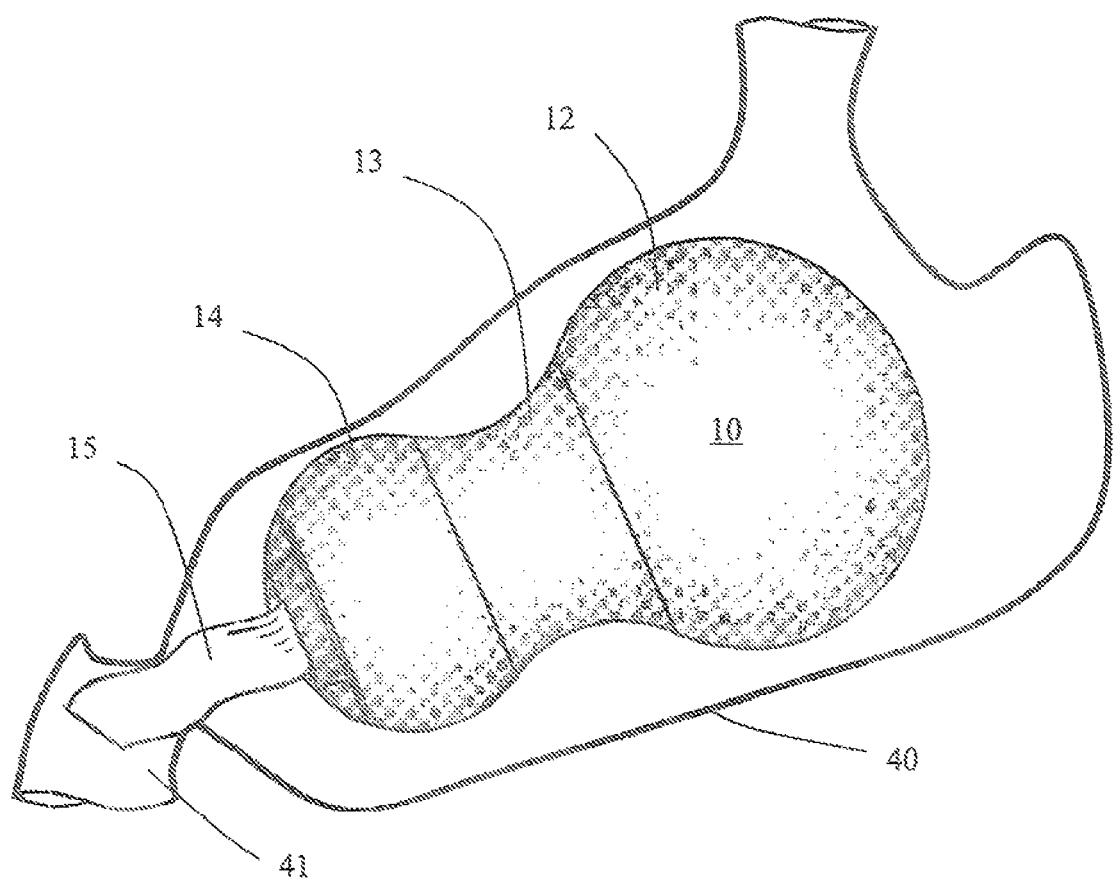
FIG. 3 shows a gastric space filler system with, two space fillers having capability for dispensing drug into intestine.
Figure 4:
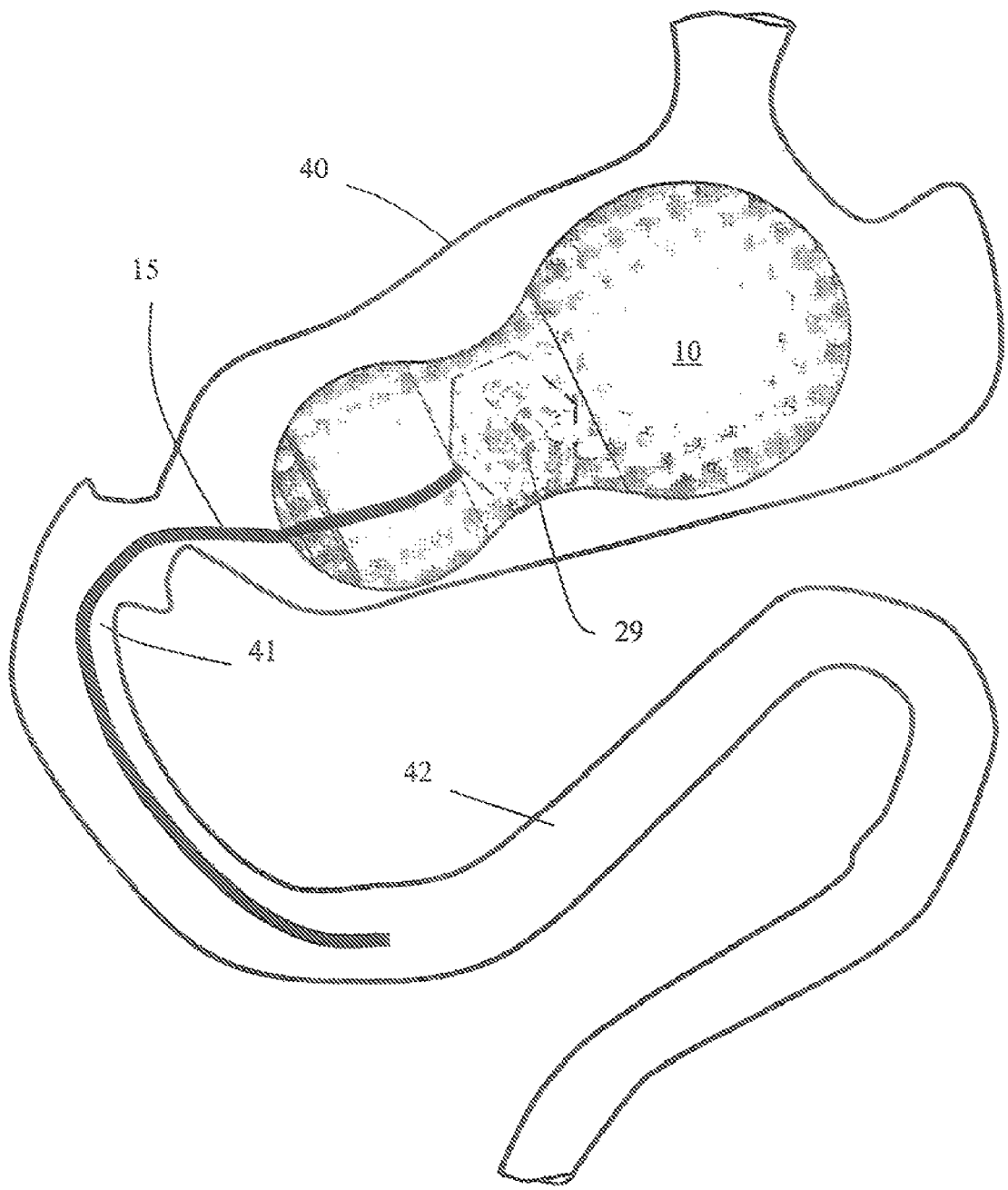
FIG. 4 shows a gastric space filler system having capability for dispensing drug with an internal pumping mechanism.

FIG. 3 shows a gastric space filler system 10 with two space fillers 12, 14 having capability of expanding, a drug dispensing section 15 for dispensing drug into the gastrointestinal system 41, whereas FIG. 4 shows a gastric space filler system 10 having capability for dispensing drug with an internal pumping mechanism 29 further into downstream portions 42 of the intestine. As described above, the internal pumping mechanism may be actuated by responding to an internal signal in the stomach 40 or be actuated by patient from outside of the body.

Figure 5:
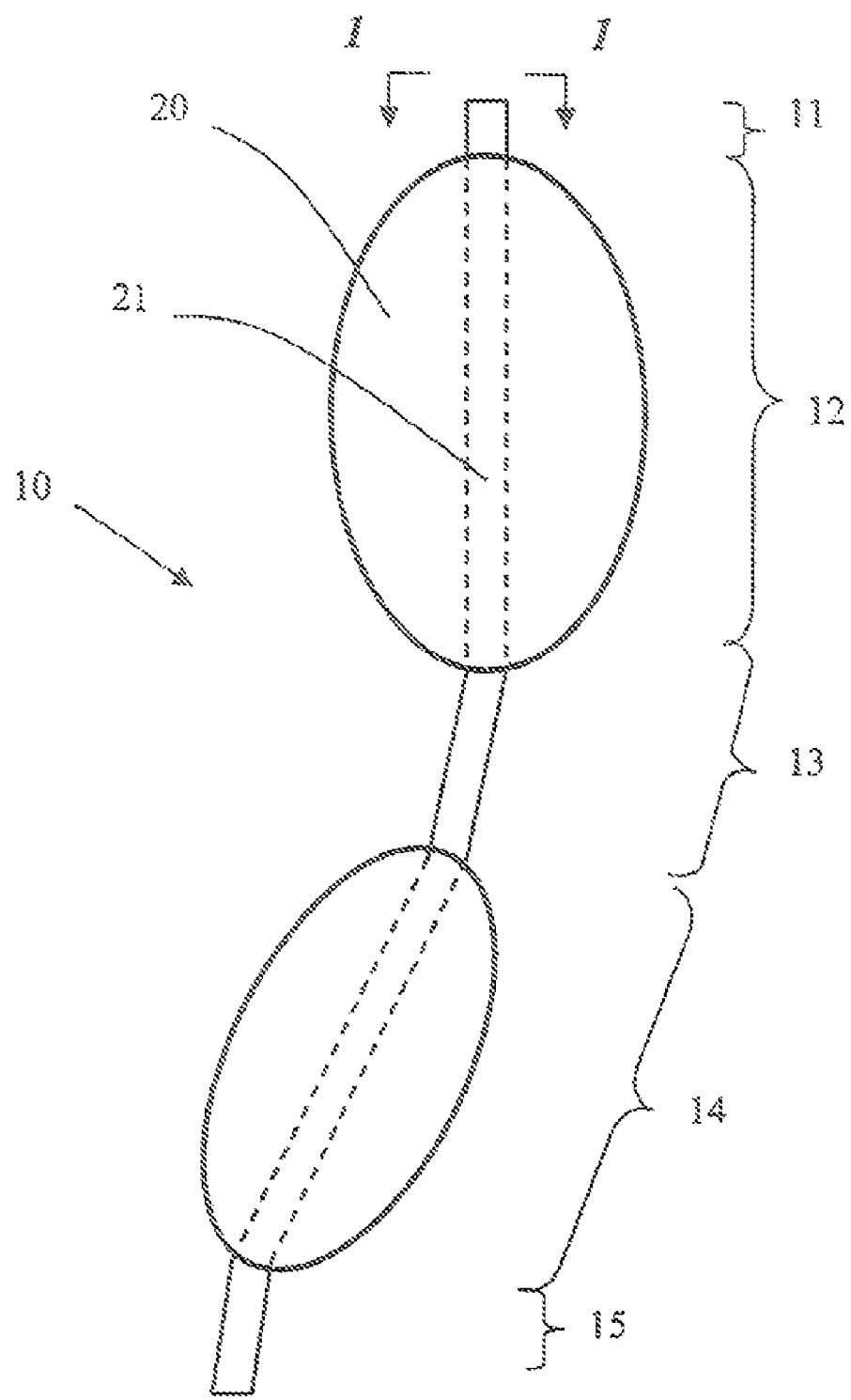
FIG. 5 shows an overall description of a 2-balloon gastric space filler system of the present invention.

FIG. 5 shows an overall view of a 2-balloon gastric space filler system 10 of the present invention. The system may comprise an entrance section 11, a first balloon section 12, a second balloon section 14, an inter-balloon section 13, and a drug dispensing section 15. In one embodiment, at least a portion of the exterior surface 20 of the balloon is treated to be hydrophilic, with anti-emetic property, or to have reduced surface friction. It is essential that the two balloons are separated with a minimum distance to prevent balloon rubbing against each other. The distance between the two balloons is sized between about 10 to 40 mm, preferably between about 20 and 30 mm. To appropriately fit the filler system into the stomach of a typical patient, the overall axial length of the double-balloon space filler is sized between about 100 and 300 mm, preferably between about 150 and 200 mm.

Figure 6A:
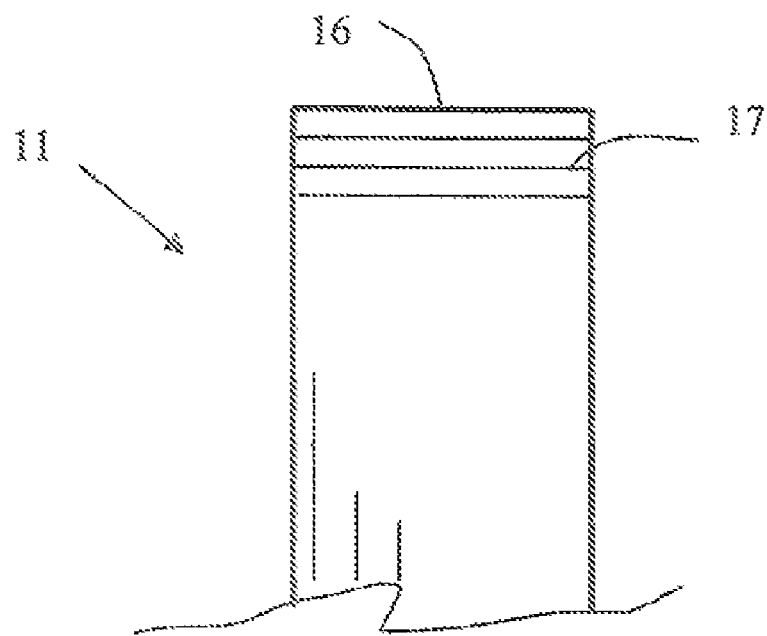
FIG. 6A shows an entrance section of the 2-balloon gastric space filler system.
Figure 6B:
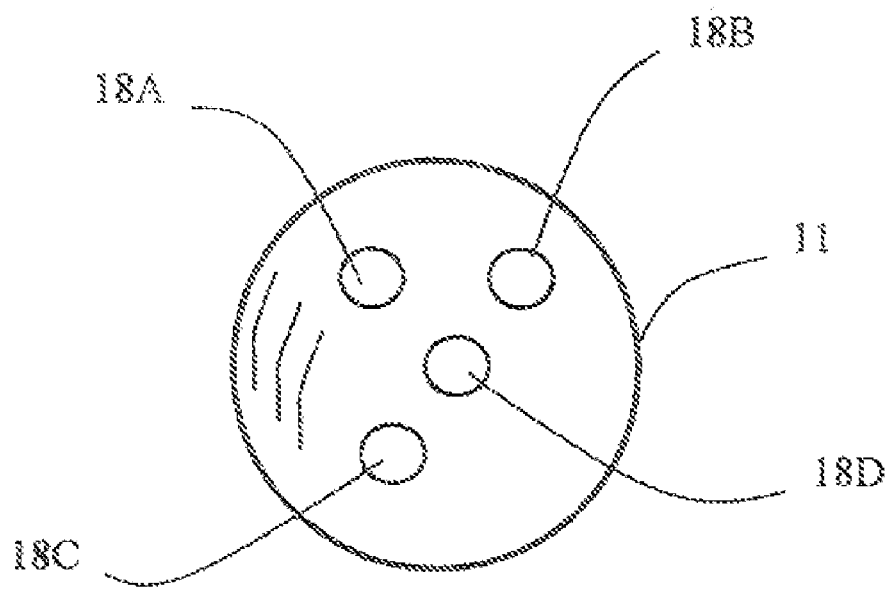
FIG. 6B shows a top cross-sectional view, section 1-1, of the entrance section of the 2-balloon gastric space filler system of FIG. 5.

FIG. 6A shows an entrance section 11 of the 2-balloon gastric space filler system whereas FIG. 6B shows a top cross-sectional view, section 1-1 of the entrance section of the 2-balloon gastric space filler system of FIG. 5. The proximal end 16 of the entrance section 11 may comprise a coupling mechanism 17 for coupling to a delivery catheter sheath, to a fluid-filling tube, or to a retrievable device. In one embodiment, the entrance section may be recessed into the first balloon to show minimal protrusion out of the balloon profile. The conduit 21 may include a plurality of lumens for fluid communication or instrument throughput. In one embodiment, the lumens have a self-sealing or unidirectional one-way valve. The lumens may include a first lumen 18A for fluid infusion into the first balloon 12, a second lumen 18B for fluid infusion into the second balloon 14, a third lumen 18C for drug infusion into the drug reservoir 27, a fourth lumen 18D for allowing an instrument (for example, a push-pull plunger) to manipulate the drug exit section 15, and other lumens, if needed.

Figure 7:
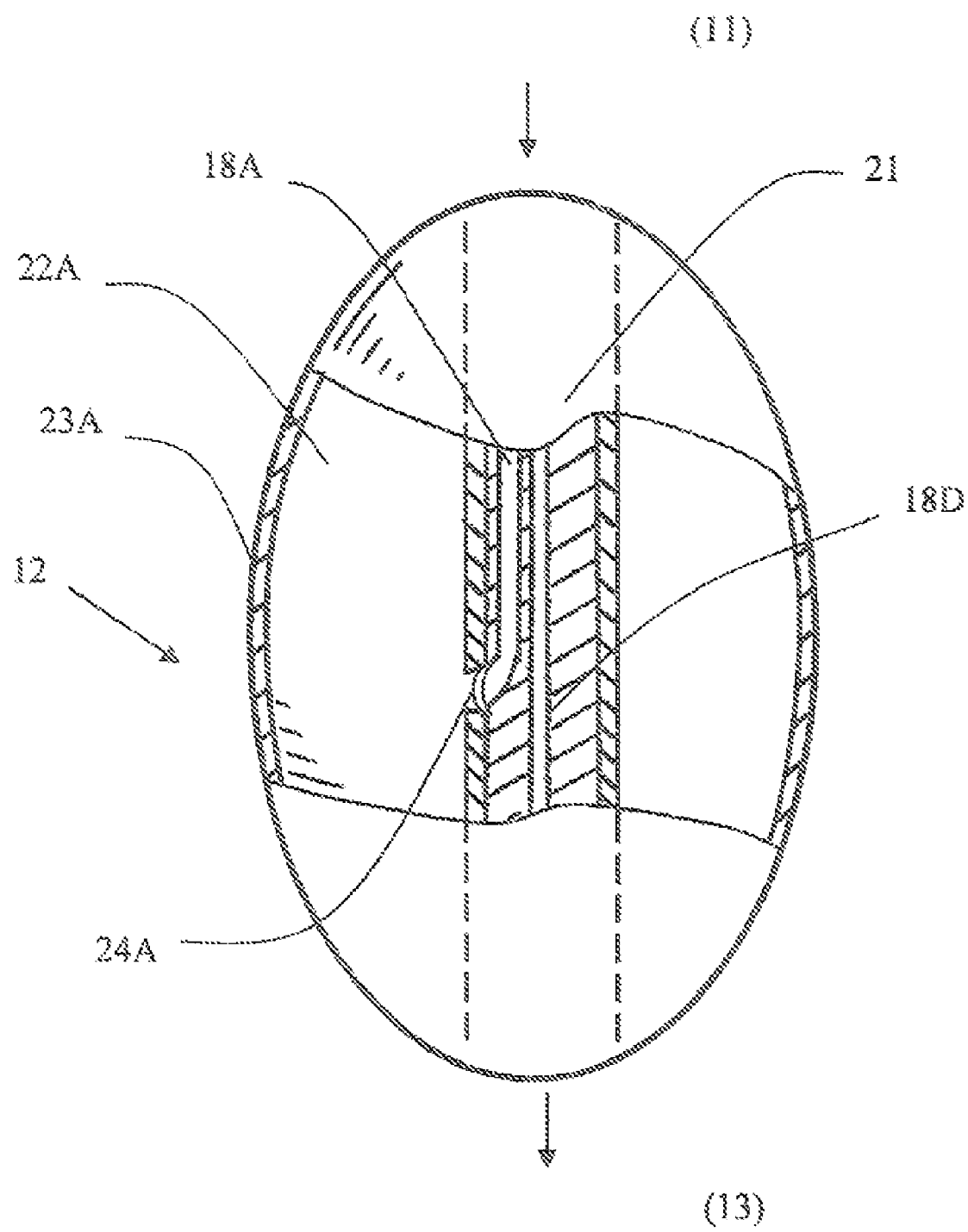
FIG. 7 shows a front cross-sectional view of the first balloon section of the 2-balloon gastric space filler system of FIG. 5.

FIG. 7 shows a front, cross-sectional view of the first balloon section 12 of the 2-balloon gastric space filler system of FIG. 5. The filling fluid is introduced into the first interior space 22A of the first balloon 12 via the lumen 18A to expand the balloon wall 23A outwardly. At the interface of the first lumen 18A and the first balloon space 22A, there provides a first unidirectional valve 24A or restriction to allow fluid for one-way flow only.

Figure 8A:
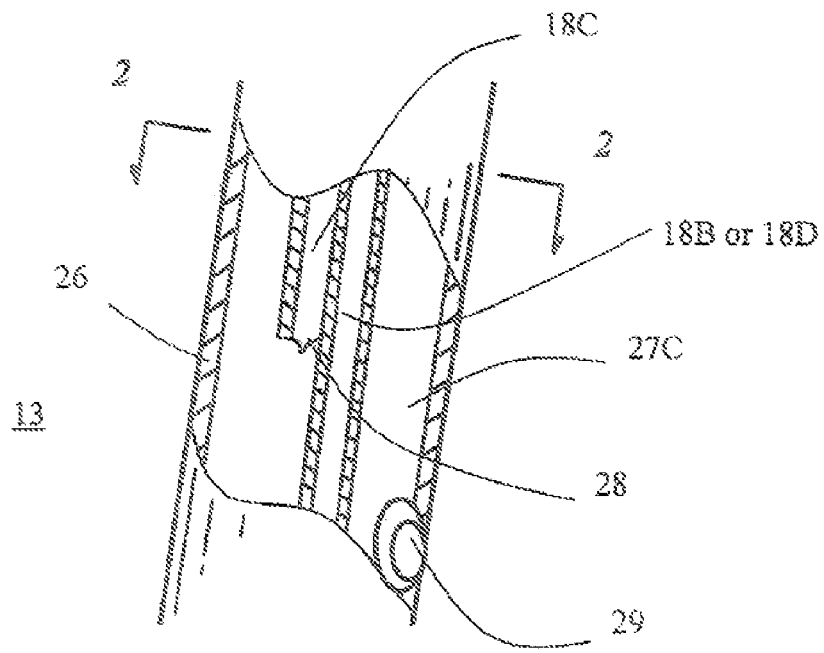
FIG. 8A shows a front cross-sectional view of the inter-balloon section of the 2-balloon gastric space filler system of FIG. 5.
Figure 8B:
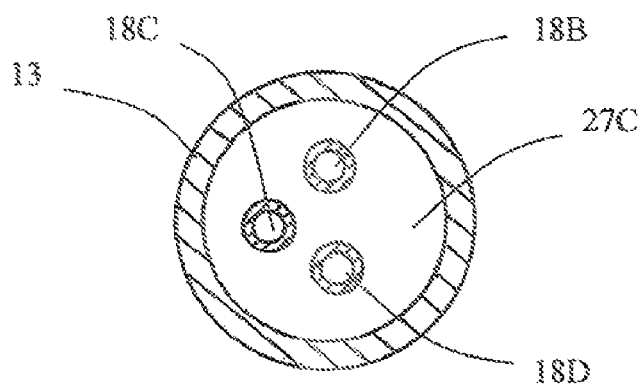
FIG. 8B shows a top cross-sectional view, section 2-2 of the inter-balloon section of FIG. 8A.
Figure 9:
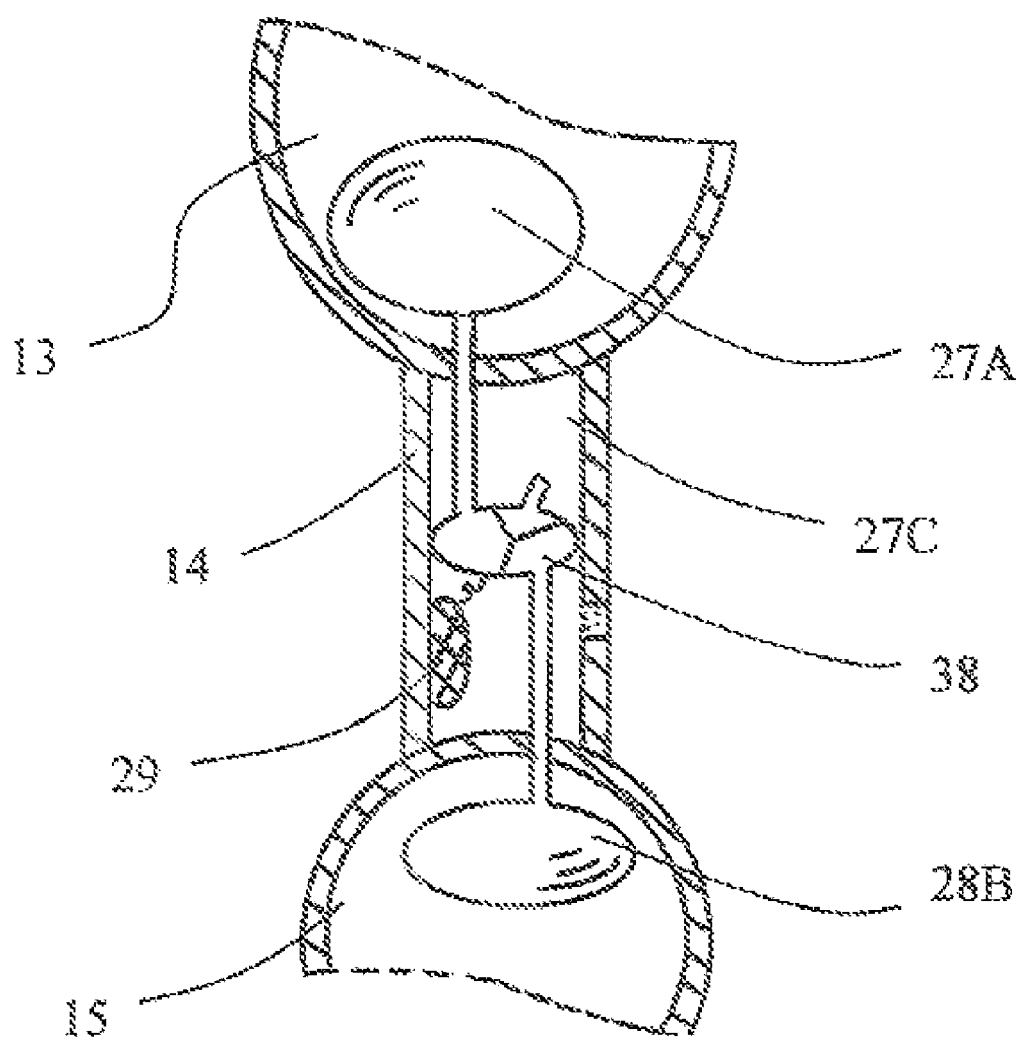
FIG. 9 shows an alternate embodiment of multiple drug reservoirs.

FIG. 8A shows a front, cross-sectional view of the inter-balloon section 13 of the 2-balloon gastric space filler system of FIG. 5, whereas FIG. 8B shows a top cross-sectional view, section 2-2 of the inter-balloon section of FIG. 8A. In one embodiment, the inter-balloon section 13 comprises a flexible elongate zone including a sheath wall 26 that connects the first balloon to the second balloon. The flexible elongate zone may be made of material selected from balloon-compatible polymers, for example, polyethylene, polystyrene, polyurethane, silicone, fluoro-polymer, co-polymers thereof and the like.

A portion of the inter-balloon section forms a closed space that serves as a drug reservoir 27C, wherein the third lumen 18C for drug infusion is in one-way fluid communication to the reservoir with a unidirectional restriction 28. An optional pumping mechanism 29 is conveniently located at or adjacent the inter-balloon section to release drug through the ports on the sheath wall 26 or through the vent ports 30 on the drug dispensing section 15. In one embodiment, the ports on the sheath wall or on the drug dispensing section are equipped with unidirectional features for drug release out of the filler system. In one embodiment, the pumping mechanism is powered by an embedded battery or power-generating source. In another embodiment, the pumping mechanism is equipped with a remotely rechargeable power-generating element, such as the one recharged via electromagnetic energy, or ultrasound energy.

Figure 10:
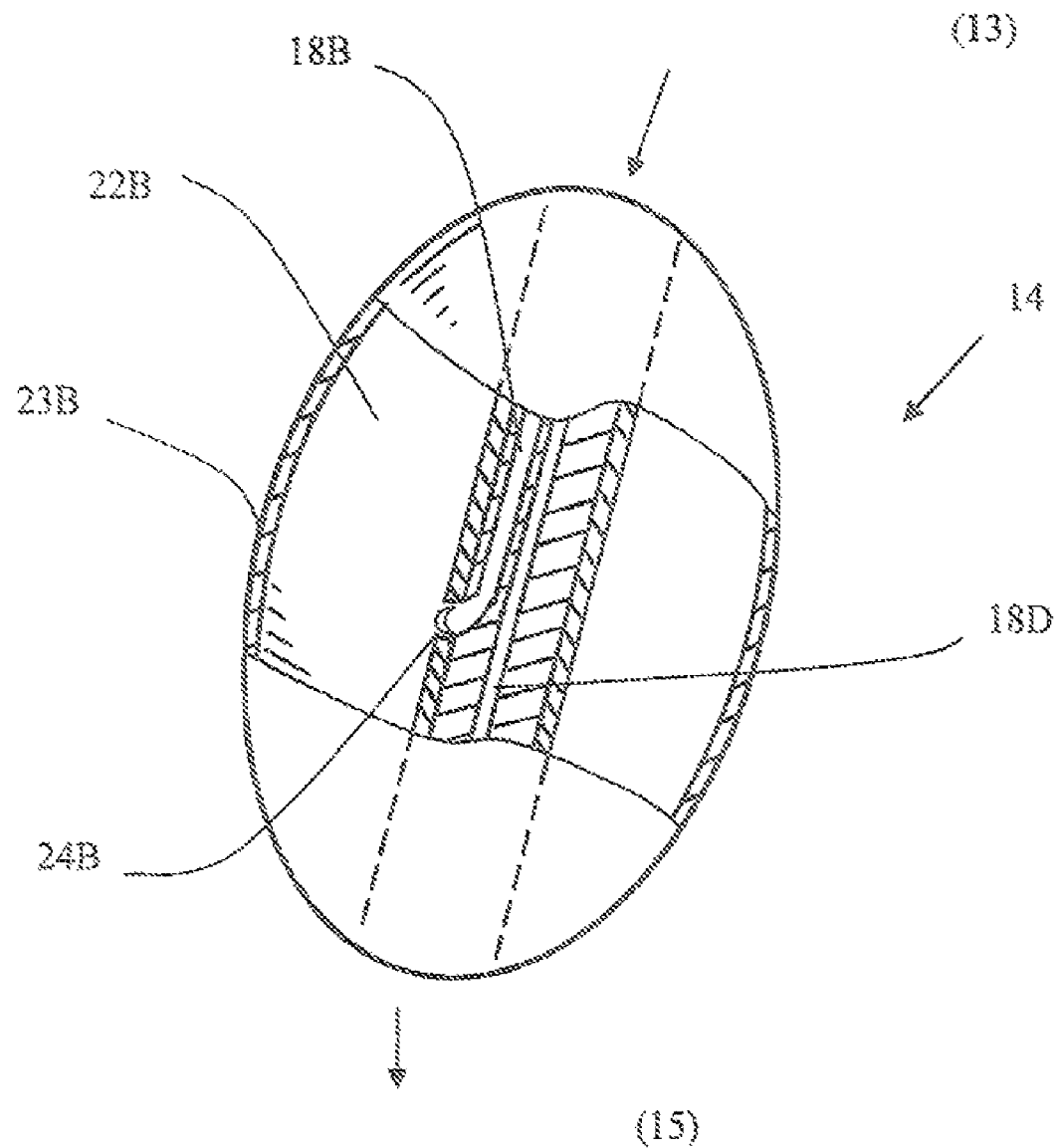
FIG. 10 shows a front cross-sectional view of the second balloon section of the 2-balloon gastric space filler system of FIG. 5.

FIG. 10 shows a front cross-sectional view of the second balloon section 14 of the 2-balloon gastric space filler system of FIG. 5. As mentioned, the filling fluid is introduced into the second balloon space 22B of the second balloon 14 via the second lumen 18B to expand the balloon wall 23B outwardly. At the interface of the second lumen 18B and the second balloon space 22B, there provides a second unidirectional valve 24B or restriction to allow fluid for one-way flow only.

In one embodiment, the drug reservoir of the present invention may be a closed space in the inter-balloon section, or may be a pouch conveniently located within either the first or the second balloon. In another embodiment, the first balloon and the second balloon may also be in fluid communication through a bi-valve. In an alternate embodiment FIG. 9, the first drug reservoir pouch 27A in the first balloon, the second drug reservoir pouch 27B in the second balloon and the drag reservoir 27C in the inter-balloon section may be in controlled fluid communication through a tri-valve 38 that is optionally actuated by a pumping mechanism 29. In one embodiment, the drug reservoir may be re-filled at least once during the implantation period.

Figure 11A:
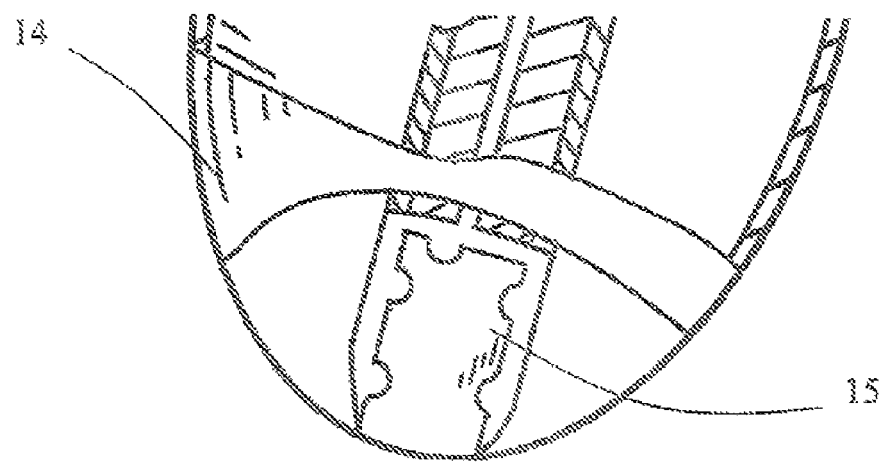
FIG. 11A shows a drug dispensing section recessed within a balloon cavity.
Figure 11B:
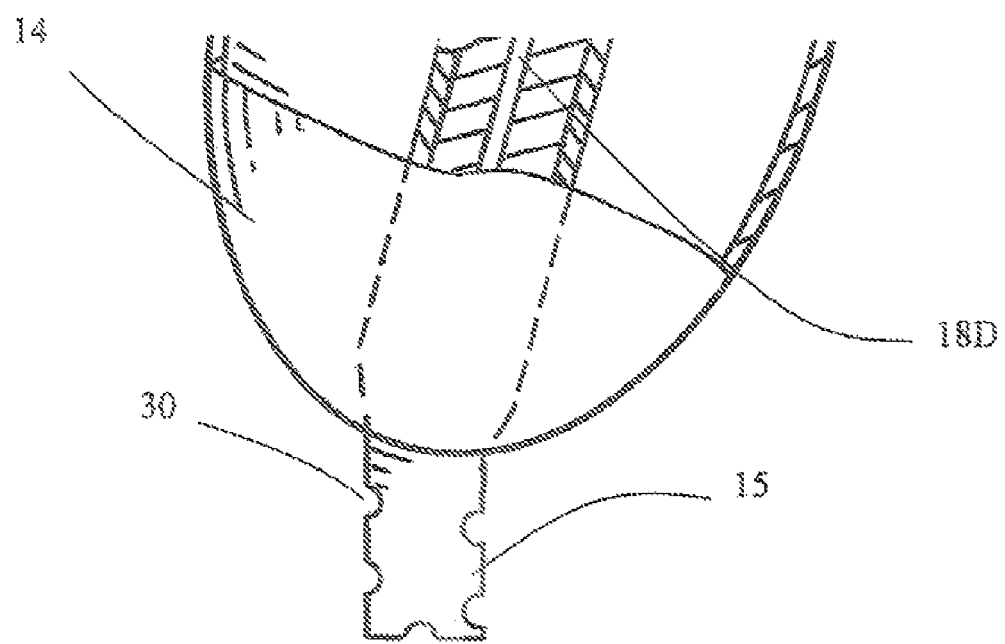
FIG. 11B shows a drug dispensing section extendable into the intestine region of a patient.

FIG. 11A shows a drug dispensing section 15 recessed within a balloon cavity of the second balloon 14, whereas FIG. 11B shows the drug dispensing section that protrudes outwardly and is extendable into the intestine region of a patient. The drug dispensing section may have a plurality of vent ports 30 appropriately located around the dispensing section 15.

Figure 12:
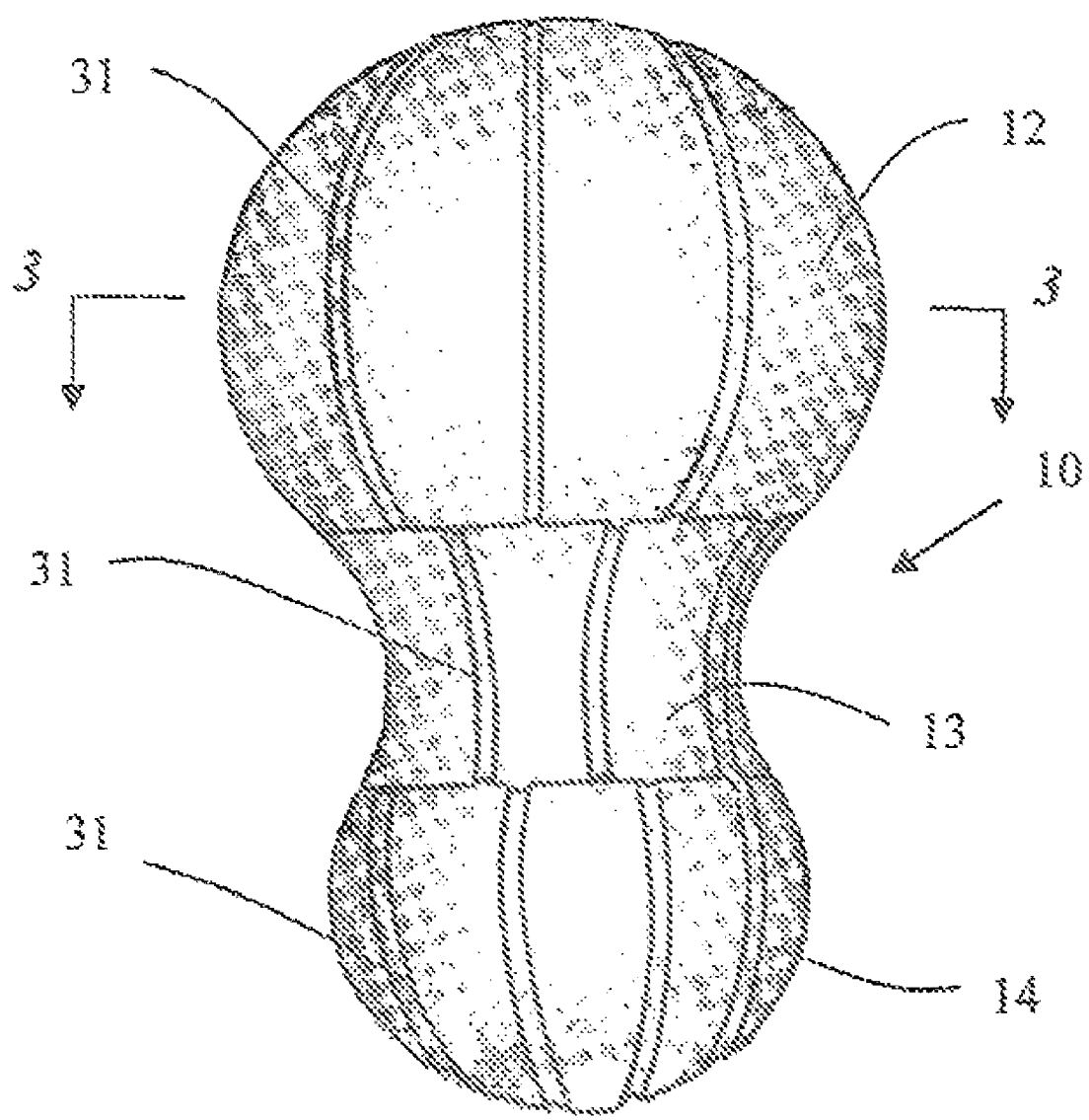
FIG. 12 shows a perspective view of the space filler device with self-releasing drug reservoir.
Figure 13:
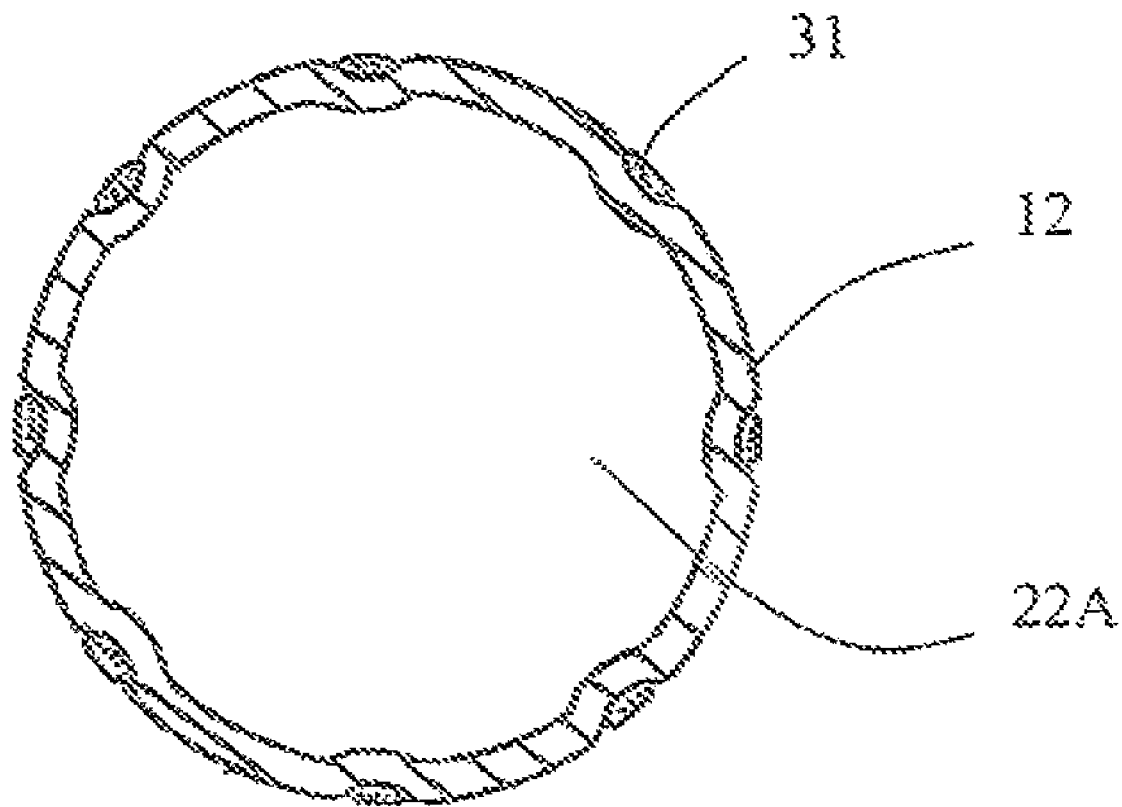
FIG. 13 shows a top cross-sectional view, section 3-3 of the space filler device of FIG. 12.

In a sustained drug delivery system, FIG. 12 shows a perspective view of the space filler device 10 with self-releasing drug reservoir. The exterior surface of the system, including the first balloon 12, the second balloon 14 and the inter-balloon section 13 may be sized and configured to have a plurality of coating zones 31. In one example, the coating zone is a trough-like or groove-like zone that could hold substantial amount of drug-containing coat. FIG. 13 shows a top cross-sectional view, section 3-3 of the space filler device of FIG. 12. The overall profile of the balloon including the coating zone is substantially equivalent to the original exterior profile of the balloon. In some aspects, the drug-containing coat is biodegradable that is sized and configured to biodegrade at a specified rate and time duration. In one embodiment, the coating material is elastomeric material comprising a high percentage of voids or micropores, like a sponge or foam for sustained drug diffusion.

Figure 14:
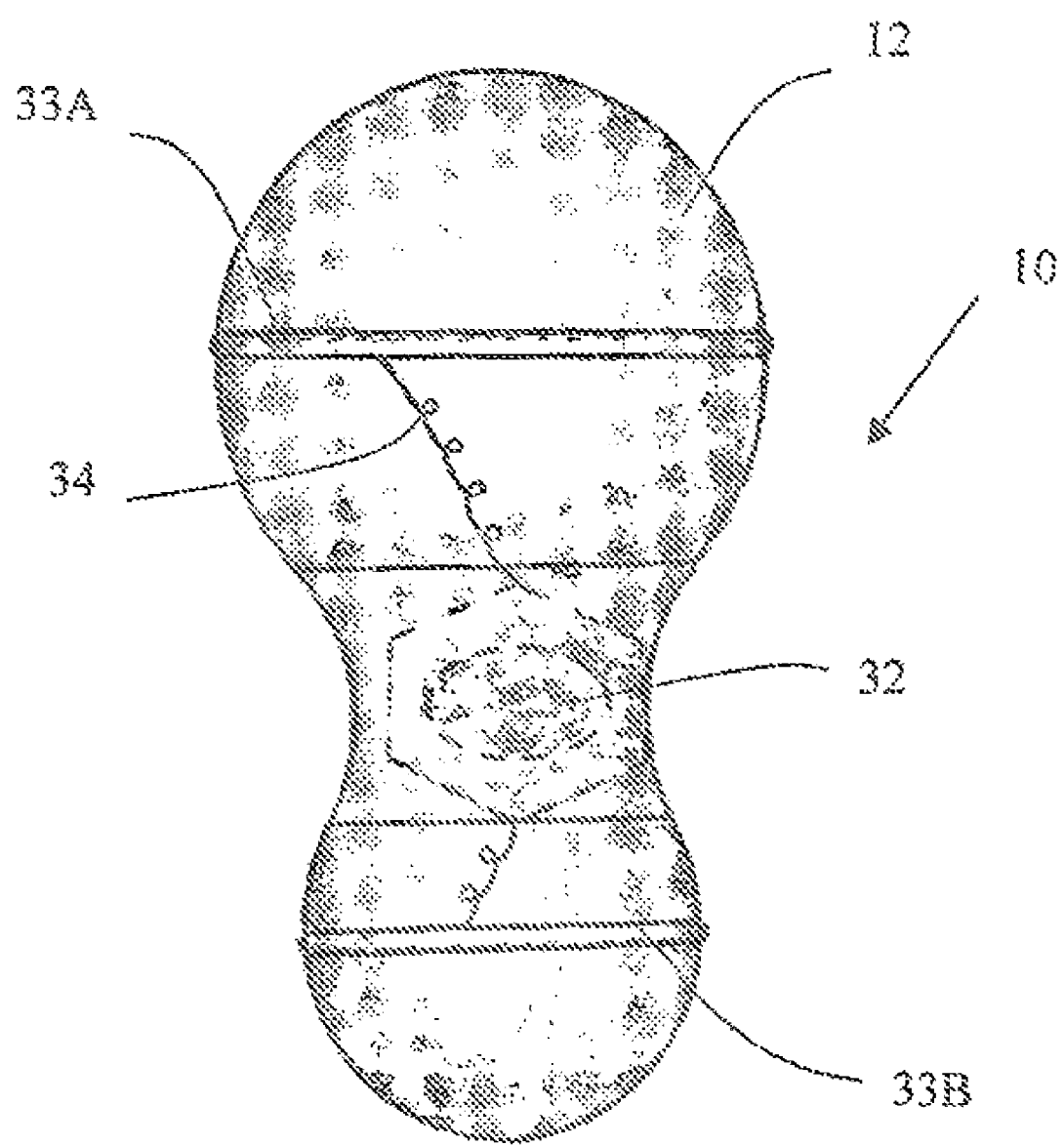
FIG. 14 shows a perspective view of the space filler device with electric stimulation capability.

FIG. 14 shows a perspective view of the space filler device 10) with electric stimulation capability. In one embodiment, there provides an electrode 33A, 33B at the outermost circumference of the balloon. The electrode may be a point electrode, a line electrode, a ring-like electrode, an area electrode, or the like that is connected to a power generator 32 via an insulated conductor 34. The power generator could provide radiofrequency energy for nerve stimulating or hormonal secretion purposes. The electrode is generally made of flexible conductive material, such as metallic mesh, metallic wires, or conductive elastomeric silicone. It is known to one ordinary skilled in the art that a conductive silicone may be made of elastic silicone with adequately dispersed metallic particles.

One prior device for achievement of weight loss that has received regulatory approval in the EU and made it through late-stage clinical trials in the US is Medtronic's gastric stimulation system. The results so far with this device have been disappointing, and the pivotal U.S. trials did not meet the pre-specified endpoint of effectiveness. In general, the device produces disorganized motion within the stomach of patients with normal motility, and nausea appears to be a significant issue. There appears substantial room for improvement within these types of devices, and that it will be worthwhile to test a variety of electrodes, a variety of positions for the electrodes and variation in the strength and rhythm of the electrical pulses being applied. One specific aspect of the present invention is to provide a balloon preferably a double-balloon) system with electrodes arranged and spaced apart in certain particular pattern for gastric stimulation. Another specific aspect of the present invention is to provide a balloon system with an anchored electric stimulation subunit for intended gastric or intestine stimulation.

In one embodiment, the connecting members between the balloons for example, the inter-balloon section in FIG. 5 are made of flexible and/or elastic material. In another embodiment, the connecting members are made of solid flexible material that allows no fluid communication between the two space fillers.

The device of the present invention intends to provide mechanisms for preventing or avoiding migration, bowel obstruction, bleeding diathesis, erosion, perforation of stomach or any internal organs, and the like. Some complications are acceptable if the benefits of device design far outweigh the risks, such as access site related minor complications, some patient discomfort due to the presence of the device or due to access site related issues, nausea, feeling of bloating, and the like.

U.S. Pat. No. 6,890,300 issued on May 10, 2005, entire contents of which are incorporated herein by reference, discloses a MEMS (microelectrical mechanical systems) chip sensor based upon detection of an induced inductance in the sensor. The sensor is used in an environment for detection of fluid pressure or other marker-level (for example, a biomarker). The method and system is particularly useful in humans to sense parameter changes. For example, when excessive acid concentration is sensed using a pH sensor, a device on the balloon system is triggered to release an antacid drug, e.g., using a drug delivery pump as disclosed herein.

U.S. Pat. No. 6,939,299 issued on Sep. 6, 2005, entire contents of which are incorporated herein by reference, discloses an implantable miniaturized pressure sensor integrating a capacitor and an inductor in one small chip, wherein the capacitor has an upper capacitor plate and a lower capacitor plate connected to one or more spiral inductor coils. The sensor is micromachined from silicon to form a thin and robust membrane disposed on top of the upper capacitor plate to sense an external fluid pressure. The resonant frequency of the sensor can be remotely monitored and continuously measured with an external detector pickup coil disposed proximate the sensor.

U.S. Pat. No. 7,131,945 issued on Nov. 7, 2006, entire contents of which are incorporated herein by reference, discloses a wireless intraocular pressure sensor device for detecting excessive intraocular pressure above a predetermined threshold pressure, comprising: a pressure switch that is sized and configured to be placed in an eye, wherein the pressure switch is activated when the intraocular pressure is higher than the predetermined threshold pressure; and an optical output configured to be placed in the eye and electrically connected to the pressure switch, wherein the state of the optical output indicates whether the pressure switch was activated. Some aspects of the invention provide a wireless pressure sensor device for detecting intragastric pressure or pressure wave, wherein the sensor device is configured to receive a radiofrequency source from outside the body or emit radiofrequency output signal.

Some aspects of the invention provide a method for determining fluid, pressure or pressure change within a patient comprising: (a) providing a wireless capacitive MEMS chip sensor comprising an inductance coil and spaced apart capacitor plates as an inductive-capacitive circuit, with the fluid in pressure contact with one of the capacitive plates; (b) inducing a mutual inductance as an external signal into the sensor to produce the resonant frequency response as an internal signal from the sensor; and (c) determining the fluid pressure within the patient externally of the patient from the internal signal as a function of the resonant frequency response from the sensor resulting from a change in capacitance of the sensor due to a variation in the spacing of the plates produced by the fluid pressure of the fluid from the sensor resulting from the change in the series resistance. A pressure sensor element and methods of use are well known to one skilled in the art, for example the MEMS unit disclosed in U.S. Pat. No. 6,890,300 or U.S. Pat. No. 6,939,299.

Space Filler with Drug Release Features

A 2-balloon space filler system with a functional device is provided, wherein the device may be endoscopically attached to the inner stomach wall. The functional device may have one or more therapeutic or diagnostic functions. The device may be used for long or short term monitoring or therapies of gastrointestinal and other physiological and clinical conditions. The device can be used for diagnostic or therapeutic applications such as pH monitoring, pressure monitoring, temperature monitoring, electromyogram recording, electrogastrogram recording, electrical stimulation, gastric pacing, substance or drug delivery (e.g. medication or gene therapy), balloon obesity therapy, etc. Various sensors may be used, e.g., a pressure sensor, a strain gauge, a temperature sensor, a pH monitor, a sensor for sensing muscle contractions of the stomach, a sensor for sensing electrical parameters of the stomach wall, a glucose monitoring, or redox.

The sensors on the filler system may be used to sense electrical parameters, pressure, movement, and temperature. Diagnostic ultrasound may be utilized by an implanted filler device with an acoustic transducer as part of the balloon filler system. Other parameters may be measured to determine conditions of the stomach or effectiveness of treatment such as electrical stimulation. The device may be used to treat various stomach conditions including gastric motility disorders, to deliver drugs or substances at a desired or predetermined rate (e.g. a slow release or localized drug treatment), and/or to treat obesity. The device may be used for electrical stimulating a muscle layer of the stomach wall or associated nerves of the stomach. An externally transmitted telemetric signal (for example, electromagnetic) may be used to actuate treatment. For example, the release of the medication or other substance may be actuated by an external RF signal received by electronics in the device housing on the filler system. Sensed diagnostic information may also be transmitted from the implanted device to an external receiver/controller that may record or evaluate the sensed information.

Some aspects of the invention provide a pressure sensor element to be mounted on at least one balloon of the 2-balloon gastric space filler system for sensing an intragastric pressure. In one embodiment, the pressure sensor element further comprises a transmitter for wirelessly transmitting the measured pressure to a receiver outside a body of the patient or recipient. In another embodiment, the pressure sensor element transmits the measured pressure to an actuator of the drug-releasing pump installed at the drug reservoir.

Some aspects of the invention provide a multi-balloon space filler as disclosed in U.S. patent application Ser. No. 11/315,925 filed Dec. 22, 2005 with optionally drug delivery features and/or electrical stimulation features. In one embodiment, each of the multi-balloon space filler system is to be filled with infusing fluid independently. In another embodiment, at least one balloon serves a drug reservoir.

A balloon-like space filler could generally be manufactured by dip coating a mandrel into silicone solution a few times to build up the thickness. For connecting a balloon-like space filler with another space filler, silicone compatible adhesive is generally used, for example, RTV silicone or moderate temperature curing silicone adhesive.

In one embodiment, at least a portion of the space filler device is ultrasonically visible. In another embodiment, an ultrasonic transducer is mounted on the space filler for emitting an ultrasonic signal for viewing.

In one embodiment, the gastric space filler device is configured to be deliverable through an esophagus of the patient. In another embodiment, at least a portion of an external surface of the space filler device is treated with an anti-acid substance, or an anti-adhesion substance. The space filler should be able to be increased in size over time through port infusion or re-docking infusion. When a valve is used as an infusing port, the valve could be put into a recess or in low profile, so it may not contact walls of stomach. The size of the space filler can be adjusted over time to allow initial acceptance by the stomach and increased volume to get the right balance of weight loss and the lack of nausea, bloating and vomiting.

In one embodiment, the space filler device is fabricated from polyurethane sheet material, wherein the polyurethane sheet material comprises a single layer. In a preferred embodiment, the space filler device has neither seams nor edges. In another embodiment, the space filler is made of a non-biodegradable material selected from a group consisting of polyester, polypropylene. Nylon, polyethylene, silicone, latex, polyethylene, thermoplastic elastomer (TPE), and copolymers thereof. In one embodiment, the space filler device of the present invention is a permanent implant. In another embodiment, the space filler device of the present invention has a useful life of about 3 to 12 months. The filler device may comprise at least one radiopaque marking, wherein the radiopaque marking may be selected from a group consisting of platinum, gold, tungsten, iodine, and the like. The radiopaque marking may also be applied by coating or taping radiopaque substance on the space filler device.

Silicone is generally a gas and water permeable membrane subject to osmotic forces. In some cases, air will quickly be resorbed by the surrounding body fluids and the device might collapse. Ionic or pressure differential forces can cause volumetric changes. In some embodiments, the material for constructing an intragastric space filler may be coated, impregnated or mixed with a non-permeable substance configured and enabled for mitigating any undesired effects due to gas or water permeability. In an illustrated embodiment, the internal space of the space filler is filled with swellable hydrogel, wherein the swellable hydrogel could be a temperature sensitive or pH sensitive hydrogel.

The gastric space filler device is sized and configured to fit the stomach volume up to 90% (preferably 95%) of the available stomach volume. In one embodiment, the balloon surface comprises a plurality of smooth-surfaced convex protrusions disposed to permit engagement of the stomach wall by the space filler only at spaced localities, for minimizing mechanical trauma of the stomach wall by the space fillers. The intragastric balloon system of the present invention does not interfere with digestion or absorption, thus it does not cause problems with diarrhea and malabsorption.

In one embodiment, at least a portion of an external surface of the space filler is treated with an anti-acid substance, erosion-resistant substance or anti-adhesion substance, wherein the substance comprises polytetrafluoroethylene, inert material, or other biological material (such as albumin, melatonin, phosphorylcholine, immobilized antibody, or proteins) that are biocompatible. Methods of treating the surface include coating, painting, dipping, impregnation, and the like. In one embodiment, the melatonin or PC (phosphorylcholine) coating is on at least a portion of the outer surface of the space filler. In one preferred embodiment, the melatonin or phosphorylcholine coating is on at least a portion of the outer surface of the space filler that intends to contact the stomach wall. In one embodiment, the surface is coated with peptides for satiety. The stomach space filler may also be made of or surface coated with polyolefin family like high density polyethylene, linear low density polyethylene, and ultra high molecular weight polyethylene, fluoropolymer materials like fluorinated ethylene propylene, polymethylpentene, polysulphons, or some elastomers such as thermoplastic polyurethanes and C-Flex type block copolymers.

Melatonin may reduce the pain associated with irritable bowel syndrome (Gut 2005; 54:1402-1407). As is known to one ordinary skill in the art, melatonin is a sleep promoting agent that is involved in the regulation of gastrointestinal motility and sensation. In some prior clinical experiment, melatonin was orally administered 3 mg at bedtime for two weeks, those patients with melatonin regimen showing significant attenuation in abdominal pain and reduced sensitivity in rectal pain as compared to the control group with placebo. Some aspects of the invention provide a gastric space filler device for treating obesity in a patient by reducing the stomach volume comprising, an inflatable space filler, wherein at least a portion of an external surface of the space filler device is treated with melatonin. Melatonin and/or peptides for satiety feeling may be a major component in the drug reservoir of the present invention.

Intragastric Space Filler with Stimulation Features

Electrical stimulation is generally defined herein to mean any application of an electrical signal or of an electromagnetic field to tissue of the stomach for a therapeutic or diagnostic purpose. In one embodiment, an electrical stimulation signal entrains a slow wave signal of the stomach smooth muscle that is clinically absent, weak or of an undesirable frequency or repetition rate, is sporadic or otherwise not optimal. The stimulator may be designed to trigger the spike burst electrical activity of the smooth muscle associated with smooth muscle contractions. The signals may also be designed to inhibit smooth muscle pacing potentials to reduce smooth muscle contractions. The signals may also be designed to disrupt the natural waveform and effectively alter the existing or inherent pacing.

As shown in FIG. 14, the electrode may be driven to contact the stomach wall by expanding the balloon circumference. The impedance measured is used to ensure good tissue contact with the stomach wall. Once the stomach wall is contacted, the electric stimulation is activated on demand. If the impedance indicates no tissue contact, the electric stimulation would not be activated.

The stimulator may also be designed to affect nerves associated with the stomach. In one variation, the device is designed to facilitate or expedite mixing or breaking down of food matter or liquids in the stomach. In another variation, the device is designed to control, facilitate or expedite movement of food matter or liquids through the stomach, and into the small intestine. In another variation, the device is designed to stimulate the stomach to delay passage of food from the stomach and into the small intestine. Other stimulation effects are also contemplated, including but not limited to using stimulation to treat nausea, obesity or pain symptoms. The stimulation may affect the smooth muscle contractions and/or nerves associated with the stomach.

The stimulation electrodes provide stimulation either by way of a preprogrammed pulse generator or one that is programmed or revised when the device is implanted in the stomach, e.g. based on sensed parameters or response to stimulation and/or to optimize various parameters, e.g., impedance, current density, etc. The stimulator is preferably provided with RF or other signal transmission and reception capabilities. The signal transmission capabilities may be used for telemetric communication between the stimulator and an external device, e.g. to communicate data to the external device or to receive additional programming information, command signals or stimulation signals from the external device. The stimulator may also combine the electrical stimulation feature with other therapeutic or diagnostic functions such as, e.g., drug delivery.

One embodiment of the device includes: an electronics unit containing the electronic circuitry of the device with at least one stimulating electrode that when implanted is in electrical contact with a muscle layer of the stomach wall.

One embodiment of the device includes: at least one stimulating electrode in electrical contact with the stomach wall; an electronics unit containing the electronic circuitry of the device; and an attachment mechanism for attaching the device to the stomach wall. One or more stimulating electrodes may be secured to the wall of the stomach by the attachment device. One or more stimulating electrodes may also be located on the electronics unit housing. In one embodiment, at least one stimulating electrode is embedded in the wall of the stomach. Alternatively, the housing may be removably attached to the stomach wall and removably connected to an electrode portion implanted in the stomach wall. The housing or unit containing batteries, electronics or other features, thus may be exchanged while the electrode portion or other portions remain implanted in the stomach wall, e.g. when the batteries need replacement. The electrical stimulation pulses of the device are delivered through an electronic circuit in the housing that is electrically coupled to the electrode(s). The stimulation parameters of the device can be programmed using an external programmer via telemetry.

The stimulation is provided through at least one stimulating electrode and preferably through at least one pair of bipolar electrodes. Alternatively, a remote return electrode may be provided in a monopolar device. The stimulator device may be powered by a battery included with the device or may be inductively powered, e.g. by an external source.

The stimulation device is constructed of a size and shape such that it can be deployed through the mouth and esophagus with the aid of an endoscope. As such, the stimulator is of a generally small profile, e.g. a cylindrical shape, when delivered to the implant site. In one embodiment, the electrode is a flexible ring electrode as disclosed in FIG. 14.

A functional device of the invention may be a drug delivery device. The device is attached to the balloon section and a drug pump is actuated by an electronic control signal delivered by electronic circuitry to the pump. The drug may be pumped into the stomach itself or into the intestine. The electronic circuitry may be preprogrammed to control drug or substance delivery according to a certain regimen. It may also determine its regimen based on sensed feedback. Also the parameters of the drug delivered or the control of the delivery itself may be actuated by an external control signal or by an external controller that programs the electronic circuitry via a telemetric communication.

The device components are constructed of biocompatible materials that allow it to withstand and function in the highly acidic environment of the stomach (the pH in the stomach may be, at times, as low as 1.0) for the life of the device, e.g., several weeks, months or more. The housing of the electronics unit or shell may be constructed with medical grade titanium, tantalum or alloys of these metals, which where exposed to the acidic stomach conditions, are relatively inert to the environment. Alternatively, the housing may also be constructed out of suitable inert polymers, for example, from the polyolefin family, e.g., HDPE (high density polyethylene), LLDPE (linear low density polyethylene), and PP (polypropylene), UHMWPE (ultra high molecular weight polyethylene), or fluoropolymer such as PTFE (polytetrafluoroethylene) FEP (fluorinated ethylene propylene) and other members. PMP (polymethylpentene), polysulfone, PMMA (polymethylmethacrylate) may also be used. Block copolymers may also be used or selected according to desired properties. Softer materials may be used, such as, e.g., silicones, C-Flex™, polyurethanes, co-polymer nylons (e.g. PEBAX™).

The electrodes are preferably made of corrosion resistant metals and alloys such as, e.g. platinum, iridium, gold, tantalum, titanium, stainless steel or alloys of one or more of these metals, e.g., a platinum/iridium alloy.

The electrodes may be mounted directly on the balloon, the housing, or placed on a flexible tail or tether of the filler system. The electrodes are preferably coupled to the electronic circuitry through sealed electrical contacts or through leads extending into the housing through molded corrosion resistant materials such as those described above.

A preferred system of the present invention includes an endoscopic delivery system for delivering the filler system with the stimulator through the esophagus and into the stomach.

In addition to the device being capable of stimulating the stomach wall, the electrodes of the device may also be used for diagnostic purposes. For example, the electrodes may be used to sense and observe electrical activity in the stomach wall. Such sensing may be used over time to identify patterns, diagnose diseases and evaluate effectiveness of various treatment protocols. For example irregular or lack of EMG or EGG (electrogastrogram) activity may be sensed. Stimulation may be provided in response to sensed EMG or EGG activity or lack of activity.

The delivery of the filler system is preferably performed with the guidance of an endoscope and using instruments inserted through a port in the endoscope, an overtube, or along side of the endoscope. The system or device is held in place in front of the endoscope by a custom or standard endoscopic connector tool, device holding instrument, grasper, or the like. The device and endoscope are inserted into the esophagus and into the stomach. An overtube may be used with the endoscope to protect the esophagus. The overtube may also include additional instrument channels for placing instruments through the esophagus. The endoscope is steered to a position inside the stomach. Various device actuation and holding instruments may be used to perform the procedure of delivering the device to the stomach.

In one variation, sensors can be included in the device or separately for sensing various parameters of the stomach. The sensors may be mounted on the electronics unit (stimulator housing), an attachment mechanism, or by other means, for example, in an independently attached device for example attached with an anchor or within the submucosa. The stimulation device may include a mechanical sensor that senses, for example, stomach wall contractions. In one embodiment a device implanted in the stomach includes a pressure sensor that is arranged to measure pressure change due to contractions of surrounding tissue. Alternatively, electrical sensors may detect changes in impedance due to changes in wall thickness from smooth muscle contractions. Other examples of such sensors may include, for example, pH sensors, impedance sensors, pressure sensors, strain gauges, and temperature measuring devices such as a thermocouple.

The stimulation device may be programmed to deliver stimulation in response to sensing electrical parameters or other sensed parameters. For example, a pH sensor may be used to determine when food has been ingested. When the pH changes, in a manner, indicating food ingestion, the stimulation device may be instructed to deliver stimulation pulses to stimulate gastric motility. The device may also be user controlled, where the recipient of the device or treating practitioner is able to externally activate the device, for example by using an external unit which delivers a control signal via telemetry. A temperature sensor may be used, for example, to determine when food has been ingested, by a change in temperature. The device may begin stimulating the stomach upon detecting sudden change in temperature. Pressure sensors may be used to sense motility patterns, e.g. presence, strength or frequency of contractions. Mean pressure shifts may be observed to identify fundal contractility. The stimulation device may also use sensed parameters to program or reprogram the device stimulation program. For example, by measuring impedance changes through a circuit coupled to the electrodes (e.g., delivering a constant current or voltage across the electrodes to determine impedance) or determining the contractile behavior of the stomach using a strain gauge, in response to stimulation pulses, the effectiveness of the stimulation pulses may be monitored and adjusted to provide optimal response. The stimulation program may also include an automatic adjustment in response to changes in pressure measurement.

The functional devices may be powered by a battery included with the device or the functional devices may be inductively powered. All or a portion of the device may be removed and replaced for purposes of replacing a portion of the device, e.g., a battery unit. As such, the various modules of the device are provided with docking.

The stomach space filler is capable of filling up to 95% of stomach, self-adjustable or portable. It may be dialed or programmed to adjust the space filler according to input signals of pressure, volume, pH, temperature, size, electrolyte properties, etc. In one embodiment, the space filler is also equipped with failure detection mechanism, such as bleeding/ulceration detection, migration limiter etc. The adjustable or remotely adjustable stomach space filler is retrievable. The device may be designed and arranged for restrictive food intake with custom shape that either adapts to or is made to the shape and size of a given patient's stomach.

As previously disclosed, an externally transmitted telemetric signal (for example, electromagnetic) may be used to actuate treatment. The adjustment of the volume of the space filler could be performed in the physician's office based on progression of weight loss. For example, increase of the filler volume may be actuated by an external RF signal received by electronics in the device housing on the filler system to activate the in-pumping action. An embedded micropump at entrance of the space filler may be equipped with a one-way valve for fluid to enter the space filler to increase its volume under instructions from an externally transmitted telemetric signal.

In one embodiment the implantable space filler or balloon system contains no energy source (batteries). Energy and commands to operate the electrical micropump and adjust the filler volume are sent from outside the body using electromagnetic coupling. To receive the telemetric energy and signals, the filler system is linked by way of a flexible cable to an antenna placed under the patient's skin, just above the sternum. In operations, the physician places the external antenna connected to a Control Unit over the implanted antenna of the micropump, and placed over the sternum to achieve optimal electromagnetic coupling for in-pumping activity. U.S. Pat. No. 6,850,128, entire contents of which are incorporated herein by reference, teaches electromagnetic coupling principles as opposed to direct contact between conductors. A conductor on one of the lines is connected to a ground plane which is adjacent to a resonant slot. Microwave energy is coupled to the slot, thereby exciting the slot. A second conductor is on the opposite side of the ground plane from the first conductor. Microwave energy from the excited resonant slot passes to the second conductor, thereby allowing contactless interconnection between the first conductor and the second conductor as sued in the present invention.

Before in-pumping the fluid into the space filler, a patient may be fasted, followed by drinking a lot of clear liquid. Once the telemetric signal is received, a pre-determined increment amount of liquid, say 25 ml or 50 ml, is in-pumped from around the filler inside the stomach. No external fluid is directly involved in the filler adjustment operations. Upon a physician's instructions, the in-pumping can be repeated until the desired filler space is achieved, preferably via fluoro visualization or some feedback systems. The filler volume adjustment is comfortable to the patient, lasts only a few minutes, is precise, easy to perform and monitored in real-time via visualization.

In one embodiment, the longitudinal length of the first balloon (12 is between about 70 and 80 mm, preferably about 75 mm. The second balloon (14 may be expanded to a space volume of between about 100 and 400 cc, preferably between about 100 to 300 cc. In one embodiment, the longitudinal length of the second balloon is between about 60 and 70 mm, preferably about 65 mm. In a further embodiment, the radial diameter of the first balloon may be expanded to a maximum of between about 40 and 60 mm, whereas the radial diameter of the second balloon may be expanded to a maximum of between about 20 and 40 mm. In one preferred embodiment, the first balloon is substantially larger than the second balloon in the double-balloon gastric space filler of the present invention to take the advantage of substantially more space restriction at the entrance region of the stomach to create more a feeling of satiety for the obese person.

From the foregoing, it should now be appreciated that a gastric space filler device comprising at least two space fillers with drug delivery features for reducing nausea caused by intragastric balloon system has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

The invention claimed is:

1. A system for controlled drug delivery on-demand to a gastrointestinal system of a patient, the system comprising:
 a gastric space filler;
 a drug reservoir in the gastric space filler;
 a pump secured to the reservoir and configured to dispense a drug from the drug reservoir; and
 a sensor configured to receive at least one signalling parameter from an interior of a stomach of the patient, the sensor being functionally connected to the pump and configured to trigger delivery of the drug when the at least one parameter reaches a threshold of a preset value.

2. The system of claim 1, wherein the gastric space filler comprises at least two balloons and an inter-balloon section connecting the two balloons, and wherein the pump is located at the inter-balloon section.

3. The system of claim 2, wherein the inter-balloon section consists essentially of at least one material selected from a group consisting of polyethylene, polystyrene, polyurethane, silicone, fluoro-polymer, polyether-ether-ketone (PEEK), copolymers thereof, and inert ceramics comprising pyrolytic carbon material.

4. The system of claim 2, wherein at least a substantial portion of one of the at least two balloons is the drug reservoir.

5. The system of claim 1, wherein the drug is selected from a group consisting of an anti-emetic drug, anti-nausea agent, and hormones known to produce feeling of satiety.

6. The system of claim 1, wherein the sensor is selected from a group consisting of a pressure sensor, a pH sensor, a flow sensor, a temperature sensor, and an electrolyte sensor.

7. The system of claim 1, further comprising a power source connected to at least one of the pump or the sensor, and wherein the power source is a battery.

8. The system of claim 1, further comprising:
 a power source with an antenna, wherein the power source is connected to at least one of the pump or the sensor, and wherein the power source receives energy telemetrically via the antenna using electromagnetic or induction coupling.

9. The system of claim 1, wherein an operating mode of the pump is selected from a group consisting of centrifugal, axial, pulsatile, rotary, and combinations thereof.

10. The system of claim 1, wherein the drug is dispensed into a stomach-adjacent portion of an intestine of the gastrointestinal system.

11. The system of claim 10, wherein the drug is dispensed into a distal portion of the intestine.

12. A system for sustained drug delivery to a gastrointestinal system of a human patient, the system comprising:
 a gastric space filler comprising a wall having an exterior surface, wherein the gastric space filler comprises at least two balloons connected by a conduit, and wherein the gastric space filler is configured to occupy a substantial volume of a gastric cavity in the human patient in an inflated state; and
 a drug coated onto at least a portion of the exterior surface of the wall and impregnated in at least a portion of the wall, wherein the drug coating comprises a drug carrier loaded with a drug.

13. The system of claim 12, wherein the drug coating is in a form of at least one of layer, a line, or a cluster.

14. The system of claim 12, wherein the drug carrier is made of silicone or polyurethane.

15. The system of claim 12, wherein the drug carrier is biodegradable.

16. The system of claim 15, wherein the drug carrier is selected from a group of compounds consisting of lactide, glycolide, caprolactone, polydioxanone, trimethylene carbonate, polyorthoesters, and polyethylene oxide.

17. The system of claim 15, wherein the drug carrier is selected from a group consisting of collagen, chitosan, elastin, gelatin, and combinations thereof.

18. The system of claim 12, wherein at least one of the balloons of the gastric space filler comprises at least one groove on the exterior surface, and wherein a substantial portion of the at least one groove is filled with the drug formulation.

19. The system of claim 12, wherein the wall is at least partially permeable.

20. The system of claim 12, wherein the drug comprises methylene blue.

21. The system of claim 12, wherein the drug comprises mineral oil.

22. The system of claim 12 wherein the drug is configured to resist adhesion on the gastric space filler.

23. The system of claim 12 wherein the drug is configured to resist degradation of the gastric space filler.

24. The system of claim 12 wherein the conduit is configured to allow instrument throughput.

25. The system of claim 12 wherein the conduit is configured to infuse at least one of fluid and drug into at least one balloon during an implantation period.

26. The system of claim 12 wherein the at least two balloons are separated by an inter-balloon section, and wherein the inter-balloon section has a length between approximately 10 mm and approximately 40 mm.

27. The system of claim 12 wherein the gastric space filler has an axial length between approximately 100 mm and approximately 300 mm.

28. The system of claim 12, further comprising a coupling mechanism attached to the gastric space filler and configured to couple to at least one of a delivery catheter, a fluid filling tube or a retrieval structure.

29. The system of claim 28 wherein the coupling mechanism is recessed into the gastric space filler.

* * * * *

UNITED STATES PATENT AND TRADEMARK OFFICE
CERTIFICATE OF CORRECTION

Page 1 of 2

PATENT NO. : 8,226,602 B2
APPLICATION NO. : 11/694536
DATED : July 24, 2012
INVENTOR(S) : Rodolfo C. Quijana et al.

It is certified that error appears in the above-identified patent and that said Letters Patent is hereby corrected as shown below:

On the Title page, in field (57), in column 2, in "Abstract", line 3, delete "drag" and insert -- drug --, therefor.

On page 3, in column 1, under "Other Publications", line 1, delete "Ballon" and insert -- Balloon --, therefor.

In column 1, line 39, delete "al" and insert -- al. --, therefor.

In column 2, line 21, delete "al" and insert -- al. --, therefor.

In column 2, line 39, delete "gastronomy" and insert -- gastrotomy --, therefor.

In column 3, line 5, delete "thorough" and insert -- through --, therefor.

In column 3, line 41, delete "they, can" and insert -- they can --, therefor.

In column 3, line 64, delete "drag-releasing" and insert -- drug-releasing --, therefor.

In column 5, line 1, delete "drag" and insert -- drug --, therefor.

In column 5, line 3, delete "with, two" and insert -- with two --, therefor.

In column 5, line 36, delete "capability;" and insert -- capability. --, therefor.

In column 6, line 51, delete "balloons, or" and insert -- balloons or --, therefor.

In column 7, line 5, delete "centrifugal" and insert -- centrifugal, --, therefor.

In column 7, line 7, delete "Mortezs" and insert -- Morteza --, therefor.

Signed and Sealed this
Second Day of October, 2012

David J. Kappos
*Director of the United States Patent and Trademark Office*

CERTIFICATE OF CORRECTION (continued)
U.S. Pat. No. 8,226,602 B2

In column 8, line 25, delete "front," and insert -- front --, therefor.

In column 8, line 33, delete "front," and insert -- front --, therefor.

In column 9, line 8, delete "drag" and insert -- drug --, therefor.

In column 13, line 8-9, delete "polysulphons" and insert -- polysulfones --, therefor.

In column 13, line 54, delete "stomach, and" and insert -- stomach and --, therefor.

In column 14, line 25, delete "wail." and insert -- wall. --, therefor.

In column 14, line 64, delete "where" and insert -- were --, therefor.

In column 16, line 56, delete "embodiment" and insert -- embodiment, --, therefor.